US007282522B2

(12) United States Patent
Rho et al.

(10) Patent No.: US 7,282,522 B2
(45) Date of Patent: Oct. 16, 2007

(54) HYDROXAMIC ACID DERIVATIVES AND THE METHOD FOR PREPARING THEREOF

(75) Inventors: Ho-Sik Rho, Suwon-si (KR); Heung-Soo Baek, Seoul (KR); Su-Jong Kim, Yongin-si (KR); Su-Nam Kim, Suwon-si (KR); Byung-Geun Chae, Seoul (KR); Byoung-Seok Lee, Suwon-si (KR); Bae-Hwan Kim, Suwon-si (KR); Gyu-Ho Choi, Yongin-si (KR); Eui-Dong Son, Suwon-si (KR); Hae-Kwang Lee, Yongin-si (KR); Hye-Won Lee, Yongin-si (KR); Jun-Cheol Cho, Suwon-si (KR); Duck-Hee Kim, Seoul (KR); Ih-Seop Chang, Yongin-si (KR); Ok-Sub Lee, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 10/595,124

(22) PCT Filed: Aug. 26, 2004

(86) PCT No.: PCT/KR2004/002143

§ 371 (c)(1), (2), (4) Date: Jun. 15, 2006

(87) PCT Pub. No.: WO2005/019162

PCT Pub. Date: Mar. 3, 2005

(65) Prior Publication Data

US 2006/0252834 A1    Nov. 9, 2006

(30) Foreign Application Priority Data

Aug. 26, 2003  (KR) .................... 10-2003-0059177
Mar. 25, 2004  (KR) .................... 10-2004-0020401
Jul. 14, 2004   (KR) .................... 10-2004-0054886

(51) Int. Cl.
*A61K 31/19*   (2006.01)
*C07C 259/04*  (2006.01)

(52) U.S. Cl. .............. 514/575; 562/621; 562/622
(58) Field of Classification Search .............. None
See application file for complete search history.

(56) References Cited

U.S. PATENT DOCUMENTS 5,700,811 A      12/1997  Breslow et al.
2002/0172967 A1  11/2002  Gaedek et al.

FOREIGN PATENT DOCUMENTS

JP   10-182583     *  7/1998
JP   10-182583  A     7/1998
WO   WO98/36742 A1   8/1998

OTHER PUBLICATIONS

D. Zacheis, et al., "Heteroarotinoids Inhibit Head and Neck Cancer Cell Lines in Vitro and in Vivo Through Both TAT and RXR Retinoic Acid Receptors", *J. Med. Chem.*, 1999, 42, 4434-4445.
H. Kagechika, et al., "Retinobenzoic Acids. 1. Structure-Activity Relationships of Aromatic Amides with Retinoidal Activity", *J. Med. Chem.*, 1988, 31, 2182-2192.
E. Schwartz, et al., "Topical All-Trans Retinoic Acid Stimulates Collagen Synthesis In Vivo", *The Journal of Investigative Dermatology*, vol. 96, No. 6, Jun. 1991, pp. 975-978.
S. Kang, "Photoaging and Tretinoin", *Dermatologic Clinics*, vol. 16, No. 2, Apr. 1998, pp. 357-364.
M. Ebisawa et al., "Novel Retinoidal Tropolone Derivatives. Bioisoteric Relationship of Tropolone Ring with Benzoic Acid Moiety in Retinoid Structure", *Chem. Pharm. Bull.*, vol. 49, No. 4, 2001, pp. 501-503.

* cited by examiner

*Primary Examiner*—Paul A. Zucker
(74) *Attorney, Agent, or Firm*—Sughrue Mion, PLLC

(57) ABSTRACT

The present invention provides hydroxamic acid derivatives which have anti-aging efficacy and a method for preparation thereof. It is further provided skin-care external compositions for preventing skin aging, containing the hydroxamic acid derivatives represented by the formula (I) as an active ingredient.

7 Claims, No Drawings

HYDROXAMIC ACID DERIVATIVES AND THE METHOD FOR PREPARING THEREOF

FIELD OF THE INVENTION

The present invention relates to hydroxamic acid derivatives represented by the following formula (I), having anti-aging efficacy and to a method for the preparation thereof:

[Formula 1]

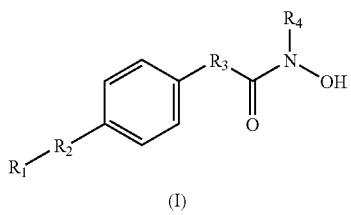

(I)

wherein,
$R_1$ is

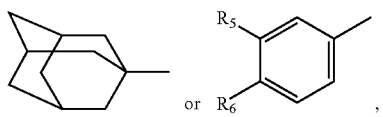

herein, $R_5$ and $R_6$ each independently represents a hydrogen atom, an alkyl group having from 1 to 10 carbon atoms or a cyclic alkyl group having from 3 to 6 carbon atoms;
$R_2$ is CONH, NHCO, $CONR_7$ or $NR_7CO$, herein, $R_7$ represents an alkyl group having from 1 to 10 carbon atoms;
$R_3$ is —$(CH)_n$—, herein, n=0 or 1; and
$R_4$ is a hydrogen atom or an alkyl group having from 1 to 10 carbon atoms.

BACKGROUND OF THE INVENTION

The skin of all living things grows aged as it grows older. In order to delay this skin aging, many efforts have been made extensively. As a result, the questions on the essence and cause of the aging have always been raised. Skin aging is classified into two kinds depending on its cause. The first is intrinsic aging that the structure of and the physiological function of the skin decline successively as aging goes on. And, the second is extrinsic aging that is caused by accumulated stress such as UV radiation. Particularly, UV radiation is well-known cause of aging. In case of the skin exposed to UV radiation for a long time, stratum corneum of the skin becomes thicker and collagen and elastin, which are main components of the skin, get denatured so that skin loses its elasticity. Thus, skin aging is accompanied by several functional and structural changes.

As structural changes caused by skin aging, epidermis, dermis and hypoderm of the skin become thinner. And, dermal ECM (extracelluar matrix), which is in charge of skin elasticity and elongation, is experienced with its component's change. ECM is composed of two components, i.e. elastic fiber which amounts to 2~4% of total ECM and collagen which amounts to 70~80%. As skin aging goes on, the skin loses elasticity due to the reduction of collagen and elastin. These reductions are caused by several factors in biosynthesis. For example, matrix metallo proteases, such as collagenase and elastase, are expressed to decompose collagen and elastin, and the collagen content within the skin is reduced. The reduction of collagen and elastin within the dermis leads the epidermis to be rough and to lose elasticity. That is, the skin becomes aged.

In order to suppress the reductions of collagen and elastin, which are a cause of the skin elasticity reduction, some materials have been developed and used. Specially, retinoid such as retinol and retinoic acid has been known to be very effective in lessening skin wrinkles and improving skin elasticity (*Dermatology therapy,* 1998, 16, 357~364). In spite of its anti-wrinkle efficacy and elasticity-improving efficacy, retinoid has some drawbacks that only a small quantity of application causes irritation to the skin and is easily oxidized in an air due to its instability, thus there are lots of limitation in using it. In order to stabilize retinoid, many studies have been conducted. However, the irritation of retinoid onto the skin, that is troubles in safety onto the skin, remains unsolved.

Retinoid includes retinol, retinoic acid or its derivatives. It exhibits various biological activities. With regard to the skin, the efficacy on abnormal keratinization or on pimple was reported. And, with regard to the skin wrinkles, it has been known that it can promote collagen biosynthesis and inhibit the activity of collagenase, i.e. an enzyme for decomposing collagen (*The Journal of Investigative Dermatology,* 1991, 96, 975~978). In addition, retinoid can inhibit the expression of elastase, with regard to the elasticity-reduction.

Up to now, retinoid has been developed as follows:

In the first stage, simple derivatives of retinol or retinoic acid were developed. As a derivative, retinyl palmitate may be exemplified. In the next, retinoid derivative including benzoic acid was developed. This derivative is named as arotinoid (*J. Med. Chem,* 1988, 31, 2182~2192). Recently, compounds including heteroatom introduced into the benzene ring of arotinoid, called as heteroarotinoid, have been developed (*J. Med. Chem.,* 1999, 42, 4434~4445).

Retinoid was reported to exhibit biological efficacy on the skin by interacting with the intercellullar receptor called as retinoic acid receptor (*British Journal of dermatology,* 1999, 140, 12~17). The structural feature of retinoid is based on tetramethyl cyclohexane, unsaturated carbon bond and carboxylic acid. Specially, carboxylic acid moiety is essential in the action of retionids and can be easily converted into an anion when interacting with the receptor (*Chem. Pharm. Bull,* 2001, 49, 501~503).

Arotinoid includes benzoic acid substituted for carboxylic acid moiety of retinoic acid. Benzoic acid moiety can be easily ionized to act as an anion. Recent studies have synthesized derivatives including various substituents for carboxylic acid moiety. These substituent-conversions are in order to maintain original efficacy of retinoid and to lessen toxicity or irritation and instability thereof. For the purpose, many studies have been conducted.

SUMMARY OF THE INVENTION

Under these circumstances, the present inventors have conducted many studies in order to lessen skin irritation of retinoid and to provide a solution for instability in external formulations for skin care. As a result, we synthesized a novel type of retinoid, i.e. hydroxamic acid derivatives. Furthermore, we found that these hydroxamic acid derivatives had good safety to the skin and improved stability in the formulations, without skin irritation and discoloration and odorizing, caused by the conventional retinal or retinoic acid. Based on these findings, the present invention has been completed.

Therefore, an object of the invention is to provide novel hydroxamic acid derivatives, which function as a retinoid to promote collagen biosynthesis and to inhibit the expression of collagenase, i.e. an enzyme for decomposing collagen and the expression of elastase, i.e. an enzyme for decomposing elastin, and to provide a method for preparing the same.

Hydroxamic acid has been widely known as a metal chelator. Judging from the structural feature of hydroxamic acid, hydroxy group of hydroxylamine adjacent to carbonyl group forms chelation with metal cation.

In additional feature, hydroxy group of hydroxylamine can be easily converted into an anion, to be used in similar to carboxylic acid. The present inventors utilized these structural features of hydroxamic acid to synthesize a novel retinoid and found that it functioned as an agonist to retinoic acid receptor. Such a compound having the stucture of hydroxamic acid and functioning as a retinoid has not been reported yet.

[Formula 1]

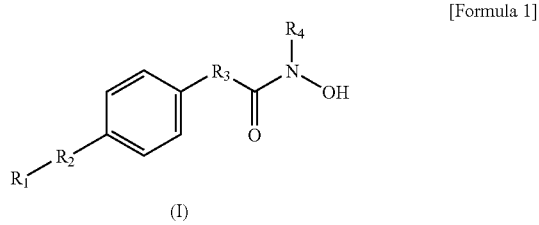

(I)

wherein, $R_1$ is

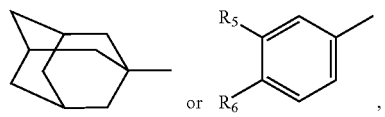

herein, $R_5$ and $R_6$ each independently represents a hydrogen atom, an alkyl group having from 1 to 10 carbon atoms or a cyclic alkyl group having from 3 to 6 carbon atoms;

$R_2$ is CONH, NHCO, $CONR_7$ or $NR_7CO$, herein, $R_7$ represents a $C_1$-$C_{10}$ alkyl group;

$R_3$ is —$(CH_2)_n$—, herein, n=0 or 1; and $R_4$ is a hydrogen atom or an alkyl group having from 1 to 10 carbon atoms.

The novel type of retinoid in the present invention, hydroxamic acid derivatives may be prepared by either of two methods exemplified below.

In detail, the method for preparing said hydroxamic acid derivatives represented by said formula (I) may comprise the steps of:

(1) Reacting benzoic acid or adamantanecarboxylic acid with methyl 4-aminobenzoate or 4-aminophenylacetic acid methylester, to form an amide bond; or reacting aniline or adamantamine wih monomethylterephthalate, to form an amide bond;

(2) Substituting an alkyl group for amide bond of benzamide formed in said step;

(3) Hydrolyzing the ester bond of benzamide or alkyl-substituted benzamide formed in said steps; and (4) Converting the acid formed by said hydrolysis to a hydroxamic acid.

Specially, in the last step of producing a hydroxamic acid derivative, one-step processing without protective/deprotective reactions is used to increase efficiency.

DETAILED DESCRIPTION OF THE INVENTION

The following is a detailed description of the present invention.

The present hydroxamic acid derivative, as a novel retinoid, may be prepared by either of two methods exemplified below.

The first method 1 may comprise the steps of:

(a) Reacting benzoic acid or adamantanecarboxylic acid with methyl 4-aminobenzoate or 4-aminophenylacetic acid methylester, to produce a benzamide compound;

(b) Substituting an alkyl group for amide bond of benzamide formed in said step;

(c) Hydrolyzing methylester of benzamide or alkyl-substituted benzamide compounds formed in said steps, to produce an acid; and (d) Reacting said acid with hydroxylamine hydrochloride or N-methyl hydroxylamine hydrochloride, to produce a hydroxamic acid derivative.

Said method of the present invention will be described in more detail by the following reaction scheme. Firstly, said method 1 may be exemplified by the following reaction scheme 1:

[Reaction Scheme 1]

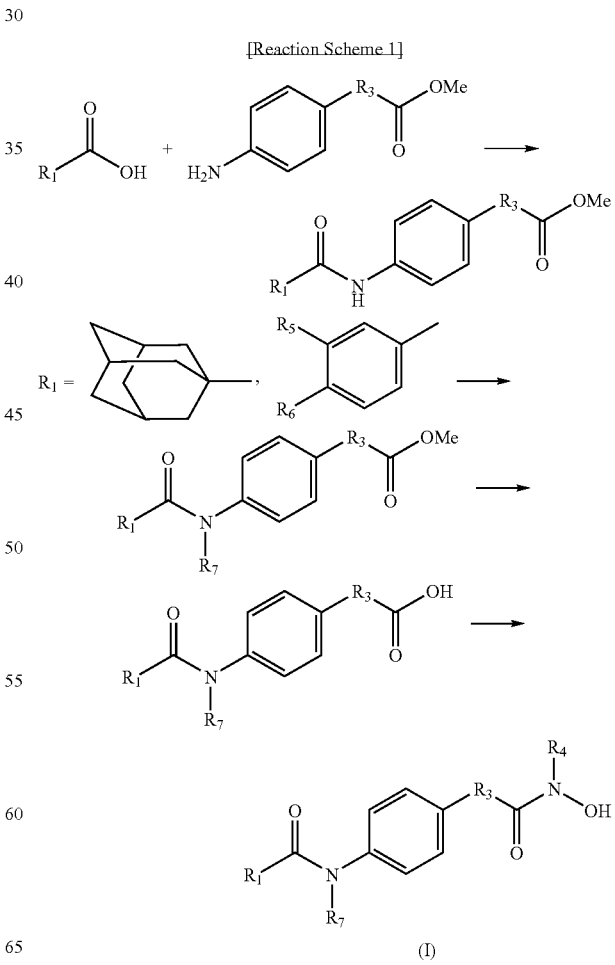

(I)

wherein, $R_5$ and $R_6$ each independently represents a hydrogen atom, a $C_1$-$C_{10}$ alkyl group or $C_3$-$C_6$ cyclic alkyl group; $R_2$ is CONH, NHCO, $CONR_7$ or $NR_7CO$, herein, $R_7$ represents a $C_1$-$C_{10}$ alkyl group; $R_3$ is —$(CH_2)_n$—, herein, n=0 or 1; and $R_4$ is a hydrogen atom or a $C_1$-$C_{10}$ alkyl group.

In the first place, benzoic acid or adamantanecarboxylic acid may be converted to an anhydride by employing ethyl chloroformate in an equivalent ratio of 1.2. A solvent employed herein may be pyridine, N-methylmorpholine and the like. Then, the anhydride may be reacted with methyl 4-aminobenzoate or 4-aminophenylacetic acid methylester, to produce a benzamide compound. A solvent employed in this reaction may be pyridine, N-methylmorpholine and the like. Additionally, in a solvent such as N,N-dimethylformamide, methylene chloride, chloroform and the like, the reaction may be performed by further employing trimethylamine, in an equivalent ratio of 1.2 to methyl 4-aminobenzoate or 4-aminophenylacetic acid methylester. Most preferably, it may be pyridine. Further, the reaction may be preferably performed at a temperature of 10~20° C. At a lower temperature than this, methyl 4-aminobenzoate or 4-aminophenylacetic acid methylester may remain unreacted and it is difficult to withdraw it from the product. While, at a higher temperature than 20° C., the anhydride may be hydrolyzed, resulting in the decrease of the yield of the product.

Benzamide compound formed herein may be reacted with an alkyl halide in a solvent of N,N-dimethylformamide, to produce a benzamide compound with an alkyl group substituted for amide bond thereof. Herein, as a base, sodium hydride may be employed in an equivalent ratio of 1.2 to benzamide. Also, alkyl halide may be employed in an equivalent ratio of 1.2 to benzamide. As an alkyl halide, it may include bromomethane, bromoethane, bromopropane, bromo-isopropane, bromobutane, bromo-tert-butane and the like.

Subsequently, methylester of benzamide with or without alkyl group substituted to amide bond may be hydrolyzed to an acid. Then, the acid formed may be converted to an anhydride by employing ethyl chloroformate. Herein, ethyl chloroformate may be employed in an equivalent ratio of 1.2 to the acid. A solvent employed herein may be pyridine, N-methylmorpholine and the like.

Then, the anhydride formed in said step may be reacted with hydroxylamine hydrochloride or N-methyl hydroxylamine hydrochloride, to produce a hydroxamic acid compound. A solvent employed in this reaction may be pyridine, N-methylmorpholine and the like. Additionally, in a solvent such as N,N-dimethylformamide, methylene chloride, chloroform and the like, the reaction may be performed by further employing triethylamine, in an equivalent ratio of 1.2 to hydroxylamine hydrochloride. Most preferably, it may be pyridine. Further, the reaction may be preferably performed at a temperature of 0~10° C. At a lower temperature than this, hydroxylamine hydrochloride or N-methyl hydroxylamine hydrochloride may remain unreacted, resulting in the decrease of the yield of the product. While, at a higher temperature than this, by-products reacting with hydroxyl group of hydroxylamine or N-methyl hydroxylamine may be produced and it is difficult to withdraw it from the product.

The other method 2 for preparing the present hydroxamic acid derivative may comprise the steps of:
(a) Reacting aniline or adamantamine with monomethylterephthalate, to produce a benzamide compound;
(b) Substituting an alkyl group for amide bond of benzamide formed in said step;
(c) Hydrolyzing methylester of benzamide or alkyl-substituted benzamide compounds formed in said steps, to produce an acid; and
(d) Reacting said acid with hydroxylamine hydrochloride or N-methyl hydroxylamine hydrochloride, to produce a hydroxamic acid derivative and may be exemplified by the following reaction scheme 2:

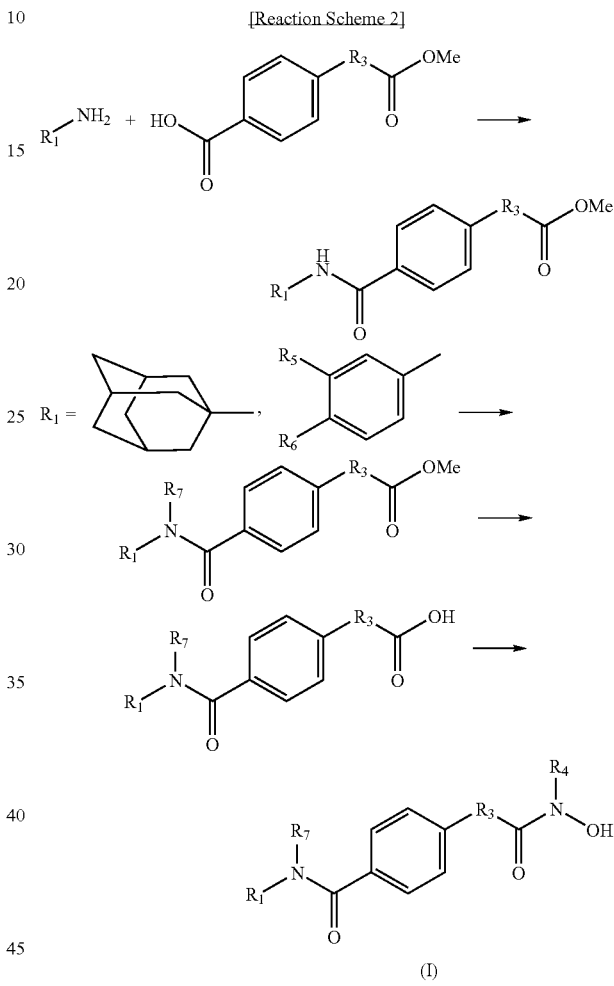

[Reaction Scheme 2]

(I)

wherein, $R_5$ and $R_6$ each independently represents a hydrogen atom, a $C_1$-$C_{10}$ alkyl group or $C_3$-$C_6$ cyclic alkyl group; $R_2$ is CONH, NHCO, $CONR_7$ or $NR_7CO$, herein, $R_7$ represents a $C_1$-$C_{10}$ alkyl group; $R_3$ is —$(CH_2)_n$—, herein, n=0 or 1; and $R_4$ is a hydrogen atom or a $C_1$-$C_{10}$ alkyl group.

As shown in the reaction scheme 2, firstly, monomethylterephthalate may be converted to an anhydride by employing ethyl chloroformate. Then, the anhydride may be reacted with aniline or adamantamine, to produce a benzamide compound. The next reactions may be performed by the same procedure described in the reaction scheme 1.

Hydroxamic acid derivatives of the formula (I) obtained in said methods may include, but not limited hereto,
1. N-[4-(N-hydroxycarbamoyl)phenyl]benzamide,
2. N-[4-(N-hydroxycarbamoyl)phenyl][4-methylphenyl]carboxyamide,
3. N-[4-(N-hydroxycarbamoyl)phenyl][3-methylphenyl]carboxyamide, 4. N-[4-(N-hydroxycarbamoyl)phenyl][4-ethylphenyl]carboxyamide,
5. N-[4-(N-hydroxycarbamoyl)phenyl][4-propylphenyl]carboxyamide,
6. N-[4-(N-hydroxycarbamoyl)phenyl][4-isopropylphenyl]carboxyamide,
7. N-[4-(N-hydroxycarbamoyl)phenyl][4-butylphenyl]carboxyamide,
8. N-[4-(N-hydroxycarbamoyl)phenyl][4-tert-butylphenyl]carboxyamide,
9. N-[4-(N-hydroxycarbamoyl)phenyl][3,4-dimethylphenyl]carboxyamide,
10. N-[4-(N-hydroxycarbamoyl)phenyl]adamantyl carboxyamide,
11. adamantyl-N-[4-(N-hydroxy-N-methylcarbamoyl)phenyl]carboxyamide,
12. N-[4-(N-hydroxycarbamoyl)phenyl]-N-methyl-benzamide,
13. N-[4-(N-hydroxycarbamoyl)phenyl]-N-methyl-[4-methylphenyl]carboxyamide,
14. N-[4-(N-hydroxycarbamoyl)phenyl]-N-methyl-[3-methylphenyl]carboxyamide,
15. N-[4-(N-hydroxycarbamoyl)phenyl]-N-methyl-[4-ethylphenyl]carboxyamide,
16. N-[4-(N-hydroxycarbamoyl)phenyl]-N-methyl-[4-propylphenyl]carboxyamide,
17. N-[4-(N-hydroxycarbamoyl)phenyl]-N-methyl-[4-isopropylphenyl]carboxyamide,
18. N-[4-(N-hydroxycarbamoyl)phenyl]-N-methyl-[4-butylphenyl]carboxyamide,
19. N-[4-(N-hydroxycarbamoyl)phenyl]-N-methyl-[4-tert-butylphenyl]carboxyamide,
20. N-[4-(N-hydroxycarbamoyl)phenyl]-N-methyl-[3,4-dimethylphenyl]carboxyamide,
21. N-[4-(N-hydroxycarbamoyl)phenyl]adamantyl-N-methylcarboxyamide,
22. adamantyl-N-[4-(N-hydroxy-N-methylcarbamoyl)phenyl]-N-methylcarboxyamide,
23. N-[4-(N-hydroxycarbamoylmethyl)phenyl]benzamide,
24. N-[4-(N-hydroxycarbamoylmethyl)phenyl][4-methylphenyl]carboxyamide,
25. N-[4-(N-hydroxycarbamoylmethyl)phenyl][3-methylphenyl]carboxyamide,
26. N-[4-(N-hydroxycarbamoylmethyl)phenyl][4-ethylphenyl]carboxyamide,
27. N-[4-(N-hydroxycarbamoylmethyl)phenyl][4-propylphenyl]carboxyamide,
28. N-[4-(N-hydroxycarbamoylmethyl)phenyl][4-isopropylphenyl]carboxyamide,
29. N-[4-(N-hydroxycarbamoylmethyl)phenyl][4-butylphenyl]carboxyamide,
30. N-[4-(N-hydroxycarbamoylmethyl)phenyl][4-tert-butylphenyl]carboxyamide,
31. N-[4-(N-hydroxycarbamoylmethyl)phenyl][3,4-dimethylphenyl]carboxyamide,
32. N-[4-(N-hydroxycarbamoylmethyl)phenyl]adamantyl carboxyamide,
33. 2-[4-(adamantylcarbonylamino)phenyl]-N-hydroxy-N-methylacetamide,
34. [4-(N-hydroxycarbamoyl)phenyl]-N-benzamide,
35. [4-(N-hydroxycarbamoyl)phenyl]-N-[4-methylphenyl]carboxyamide,
36. [4-(N-hydroxycarbamoyl)phenyl]-N-[3-methylphenyl]carboxyamide,
37. [4-(N-hydroxycarbamoyl)phenyl]-N-[4-ethylphenyl]carboxyamide,
38. [4-(N-hydroxycarbamoyl)phenyl]-N-[4-propylphenyl]carboxyamide,
39. [4-(N-hydroxycarbamoyl)phenyl]-N-[4-isopropylphenyl]carboxyamide,
40. [4-(N-hydroxycarbamoyl)phenyl]-N-[4-butylphenyl]carboxyamide,
41. [4-(N-hydroxycarbamoyl)phenyl]-N-[4-tert-butylphenyl]carboxyamide,
42. [4-(N-hydroxycarbamoyl)phenyl]-N-[3,4-dimethylphenyl]carboxyamide,
43. [4-(N-hydroxycarbamoyl)phenyl]-N-adamantyl carboxyamide,
44. N-adamantyl[4-(N-hydroxy-N-methylcarbamoyl)phenyl]carboxyamide,
45. [4-(N-hydroxycarbamoyl)phenyl]-N-methyl-N-benzamide,
46. [4-(N-hydroxycarbamoyl)phenyl]-N-methyl-N-[4-methylphenyl]carboxyamide,
47. [4-(N-hydroxycarbamoyl)phenyl]-N-methyl-N-[3-methylphenyl]carboxyamide,
48. [4-(N-hydroxycarbamoyl)phenyl]-N-methyl-N-[4-ethylphenyl]carboxyamide,
49. [4-(N-hydroxycarbamoyl)phenyl]-N-methyl-N-[4-propylphenyl]carboxyamide,
50. [4-(N-hydroxycarbamoyl)phenyl]-N-methyl-N-[4-isopropylphenyl]carboxyamide,
51. [4-(N-hydroxycarbamoyl)phenyl]-N-methyl-N-[4-butylphenyl]carboxyamide,
52. [4-(N-hydroxycarbamoyl)phenyl]-N-methyl-N-[4-tert-butylphenyl]carboxyamide,
53. [4-(N-hydroxycarbamoyl)phenyl]-N-methyl-N-[3,4-dimethylphenyl]carboxyamide,
54. [4-(N-hydroxycarbamoyl)phenyl]-N-adamantyl-N-methylcarboxyamide, and
55. N-adamantyl [4-(N-hydroxy-N-methylcarbamoyl)phenyl]-N-methylcarboxyamide.

Hydroxamic acid derivatives of the formula (I) obtained in said methods is a retinoid and function as an agonist to retinoic acid receptor and, based on retinoid's efficacy, can promote collagen biosynthesis and inhibit the expressions of collagenase, i.e. an enzyme for decomposing collagen and of elastase, i.e. an enzyme for decomposing elastin. Therefore, hydroxamic acid derivatives of the formula (I) provided by the present invention may be incorporated into medicines or external applications for improving skin elasticity.

PREFERRED EMBODIMENT OF THE INVENTION

The methods for preparing hydroxamic acid derivatives according to the present invention will be described in more detail by way of the following examples. However, these examples are provided for the purpose of illustration only and should not be construed as limiting the scope of the invention, which will be apparent to one skilled in the art.

EXAMPLE 1

Preparation of
N-[4-(N-hydroxycarbamoyl)phenyl]benzamide 20.0 g (0.16 mol) of benzoic acid was dissolved in 250 ml of pyridine and then was cooled in a ice bath of 10° C. Thereto, 23.1 g (0.21 mol) of ethyl chloroformate was added dropwise for 30 minutes. The mixture was stirred at room temperature for 2 hours and then filtered to remove salts, to give an anhydride (30.2 g, 0.15 mol). 24.1 G (0.16 mol) of metyl aminobenzoate was dissolved in 250 ml of pyridine and then was cooled in a ice bath of 10° C. Thereto, the anhydride formed in the previous step was added dropwise for 30 minutes. The mixture was stirred for another 2 hours. After distillation of the solvent, the residue was dissolved in 300 ml of ethyl acetate. The ethyl acetate solution was washed with 5% hydrochloric acid and with distilled water, dried over magnesium sulfate, decolorized with active charcoal, and then filtered. The filtrate was dried under reduced pressure, to give methyl 4-(phenylcarbonylamino) benzoate (34.7 g, 85% yield) as a pale yellow solid.

Subsequently, 34.7 g of methyl 4-(phenylcarbonylamino) benzoate was dissolved in 500 mg of methanol and thereto 50 mg of 10% KOH was added. After stirring for 3 hours, the mixture was neutralized with hydrochloric acid and then filtered, to give an acid compound, 4-(phenylcarbonylamino) benzoic acid (26.2 g, 80% yield).

4-(phenylcarbonylamino) benzoic acid formed (24.1 g, 0.10 mol) was dissolved in 200 ml of pyridine and then was cooled in a ice bath of 10° C. Thereto, 22.9 g (0.13 mol) of ethyl chloroformate was added dropwise for 30 minutes. The mixture was stirred at room temperature for 2 hours and then filtered to remove salts, to give an anhydride (38.7 g, 0.12 mol).

6.9 g (0.10 mol) of hydroxylamine hydrochloride was dissolved in 100 ml of pyridine and then was cooled in a ice bath of 10° C. Thereto, the anhydride formed in the previous step was added dropwise for 30 minutes. The mixture was stirred for another 2 hours. After distillation of the solvent, the residue was dissolved in 300 ml of ethyl acetate. The ethyl acetate solution was washed with 5% hydrochloric acid and with distilled water, dried over magnesium sulfate, decolorized with active charcoal, and then filtered. The filtrate was dried under reduced pressure, to give a final product, N-[4-(N-hydroxycarbamoyl)phenyl]benzamide (16.6 g, 65% yield) as a pale yellow solid.

TLC (in ethyl acetate:hexane=1:1); $R_f$=0.53
$^1$H-NMR(DMSO-$d_6$): δ11.23(s, 1H), 10.39(s, 1H), 9.04 (s, 1H), 8.01(m, 5H), 7.64(m, 4H).

EXAMPLE 2

Preparation of N-[4-(N-hydroxycarbamoyl)phenyl][4-methylphenyl]carboxyamide

Except that 4-methylbenzoic acid was used instead of benzoic acid, the same procedure described in Example 1 was performed to give the title compound (11.9 g, 44% yield) as a pale yellow solid.

TLC (in ethyl acetate:hexane=1:1); $R_f$=0.51
$^1$H-NMR(DMSO-$d_6$): δ11.20(s, 1H), 10.41(s, 1H), 9.07 (s, 1H), 7.94(m, 4H), 7.80(d, 2H, J=7.8Hz), 7.49(d, 2H, J=7.8 Hz), 2.33(s, 3H).

EXAMPLE 3

Preparation of N-[4-(N-hydroxycarbamoyl)phenyl][3-methylphenyl]carboxyamide

Except that 3-methylbenzoic acid was used instead of benzoic acid, the same procedure described in Example 1 was performed to give the title compound (11.2 g, 43% yield) as a pale yellow solid.

TLC (in ethyl acetate:hexane=1:1); $R_f$=0.50
$^1$H-NMR(DMSO-$d_6$): δ11.21(s, 1H), 10.39(s, 1H), 9.05 (s, 1H), 7.90(m, 6H), 7.23(m, 2H), 2.40(s, 3H).

EXAMPLE 4

Preparation of N-[4-(N-hydroxycarbamoyl)phenyl][4-ethylphenyl]carboxyamide

Except that 4-ethylbenzoic acid was used instead of benzoic acid, the same procedure described in Example 1 was performed to give the title compound (11.4 g, 39% yield) as a pale yellow solid.

TLC (in ethyl acetate:hexane=1:4); $R_f$=0.54
$^1$H-NMR(DMSO-$d_6$): δ11.20(s, 1H), 10.43(s, 1H), 9.05 (s, 1H), 7.91(m, 4H), 7.81(d, 2H, J=7.8 Hz), 7.50(d, 2H, J=7.8 Hz), 2.51(m, 2H), 1.19(m, 3H).

EXAMPLE 5

Preparation of N-[4-(N-hydroxycarbamoyl)phenyl][4-propylphenyl]carboxyamide

Except that 4-propylbenzoic acid was used instead of benzoic acid, the same procedure described in Example 1 was performed to give the title compound (12.5 g, 42% yield) as a pale yellow solid.

TLC (in ethyl acetate:hexane=1:1); $R_f$=0.55
$^1$H-NMR(DMSO-$d_6$): δ11.23(s, 1H), 10.40(s, 1H), 9.03 (s, 1H), 7.92(m, 4H), 7.83(d, 1H, J=7.8 Hz), 7.48(d, 1H, J=7.8 Hz), 2.60(m, 2H), 1.51(m, 2H), 0.95(m, 3H).

EXAMPLE 6

Preparation of N-[4-(N-hydroxycarbamoyl)phenyl][4-isopropylphenyl]carboxyamide

Except that 4-isopropylbenzoic acid was used instead of benzoic acid, the same procedure described in Example 1 was performed to give the title compound (14.3 g, 48% yield) as a pale yellow solid.

TLC(in ethyl acetate:hexane=1:1); $R_f$=0.50
$^1$H-NMR(DMSO-$d_6$): δ11.20(s, 1H), 10.41(s, 1H), 9.07 (s, 1H), 7.94(m, 4H), 7.80(d, 2H, J=7.8 Hz), 7.49(d, 2H, J=7.8 Hz), 2.80(m, 1H), 1.30(d, 6H, J=6.9 Hz).

EXAMPLE 7

Preparation of N-[4-(N-hydroxycarbamoyl)phenyl][4-butylphenyl]carboxyamide

Except that 4-butylbenzoic acid was used instead of benzoic acid, the same procedure described in Example 1 was performed to give the title compound (12.8 g, 41% yield) as a pale yellow solid.

TLC (in ethyl acetate:hexane=1:1); $R_f$=0.53
$^1$H-NMR(DMSO-$d_6$): 11.20(s, 1H), 10.42(s, 1H), 9.06(s, 1H), 7.94(m, 4H), 7.80(d, 2H, J=7.8 Hz), 7.49(d, 2H, J=7.8 Hz), 2.60(m, 2H), 1.60(m, 2H), 1.41(m, 2H), 0.95(m, 3H).

EXAMPLE 8

Preparation of N-[4-(N-hydroxycarbamoyl)phenyl][4-tert-butylphenyl]carboxyamide

Except that 4-tert-butylbenzoic acid was used instead of benzoic acid, the same procedure described in Example 1 was performed to give the title compound (11.8 g, 46% yield) as a pale yellow solid.

TLC (in ethyl acetate:hexane=1:1); $R_f$=0.51
$^1$H-NMR(DMSO-$d_6$): 11.20(s, 1H), 10.41(s, 1H), 9.07(s, 1H), 7.92(m, 4H), 7.81(d, 2H, J=7.8 Hz), 7.51(d, 2H, J=7.8 Hz), 1.25(s, 9H).

EXAMPLE 9

Preparation of N-[4-(N-hydroxycarbamoyl)phenyl][3,4-dimethylphenyl]carboxyamide

Except that 3,4-dimethylbenzoic acid was used instead of benzoic acid, the same procedure described in Example 1 was performed to give the title compound (11.9 g, 44% yield) as a pale yellow solid.

TLC (in ethyl acetate:hexane=1:1); $R_f$=0.53
$^1$H-NMR(DMSO-$d_6$): δ11.23(s, 1H), 10.40(s, 1H), 9.05 (s, 1H), 7.93(m, 3H), 7.80(d, 2H, J=7.8 Hz), 7.50(d, 2H, J=7.8 Hz), 2.47(s, 3H), 2.45(s, 3H).

EXAMPLE 10

Preparation of N-[4-(N-hydroxycarbamoyl)phenyl]adamantyl carboxyamide

Except that adamatanecarboxylic acid was used instead of benzoic acid, the same procedure described in Example 1 was performed to give the title compound (16.6 g, 65% yield) as a pale yellow solid.

TLC (in ethyl acetate:hexane=1:1); $R_f$=0.53
$^1$H-NMR(DMSO-$d_6$): δ11.22(s, 1H), 9.24(s, 1H), 8.87(s, 1H), 7.76(m, 4H), 1.96(m, 3H), 1.85(m, 6H), 1.64(m, 6H).

EXAMPLE 11

Preparation of adamantyl-N-[4-(N-hydroxy-N-methylcarbamoyl)phenyl]carboxyamide

Except that N-methyl hydroxylamine hydrochloride was used instead of hydroxylamine hydrochloride, the same procedure described in Example 10 was performed to give the title compound (11.2 g, 43% yield) as apale yellow solid.

TLC (in ethyl acetate:hexane=1:1); $R_f$=0.50
$^1$H-NMR(DMSO-$d_6$): δ9.98(s, 1H), 9.12(s, 1H), 7.55(m, 4H), 3.09(s, 3H), 1.94(m, 3H), 1.87(m, 6H), 1.62(m, 6H).

EXAMPLE 12

Preparation of N-[4-(N-hydroxycarbamoyl)phenyl]-N-methyl-benzamide

Methyl 4-(phenylcarbonylamino)benzoate (34.7 g, 0.16 mol) obtained in the intermediate step of Example 1 was dissolved in 250 ml of N,N-dimethylformamide and then was cooled in a ice bath of 10° C. Thereto sodium hydride (20.7 g, 0.16 mol) in 50 ml of N,N-dimethylformamide was added dropwise. Subsequently, bromomethane (32 g, 0.16 mol) was added dropwise to this mixture and further stirred for 1 hour. After stirring for another 2 hours, the mixture was distilled to remove the solvent and then the residue was dissolved in 300 ml of ethyl acetate. The ethyl acetate solution was washed with 5% hydrochloric acid and with distilled water, dried over magnesium sulfate, decolorized with active charcoal, and then filtered. The filtrate was dried under reduced pressure, to give methyl 4-(phenylcarbonylamino)-N-methyl-benzoate (33.5 g, 85% yield) as a pale yellow solid.

The subsequent procedures were the same as described in Example 1, to give the title compound (12.8 g, 38% yield) as a pale yellow solid.

TLC (in ethyl acetate:hexane=1:1); $R_f$=0.52
$^1$H-NMR(DMSO-$d_6$): δ11.23(s, 1H), 10.39(s, 1H), 9.04 (s, 1H), 8.01(m, 5H), 7.64(m, 4H), 3.32(s, 3H).

EXAMPLE 13

Preparation of N-[4-(N-hydroxycarbamoyl)phenyl]-N-methyl-[4-methylphenyl]carboxyamide Except that methyl 4-[(4-methylphenyl)carbonylamino] benzoate obtained in the intermediate step of Example 2 was used, the procedure described in Example 12 was performed to give the title compound (12.2 g, 44% yield) as a pale yellow solid.

TLC (in ethyl acetate:hexane=1:1); $R_f$=0.53
$^1$H-NMR(DMSO-$d_6$): δ11.21(s, 1H), 10.41(s, 1H), 9.08 (s, 1H), 7.94(m, 4H), 7.83(d, 2H, J=7.8 Hz), 7.52(d, 2H, J=7.8 Hz), 3.30(s, 3H), 2.45(s, 3H).

EXAMPLE 14

Preparation of N-[4-(N-hydroxycarbamoyl)phenyl]-N-methyl-[3-methylphenyl]carboxyamide Except that methyl 4-[(3-methylphenyl)carbonylamino] benzoate obtained in the intermediate step of Example 3 was used, the procedure described in Example 12 was performed to give the title compound (12.2 g, 44% yield) as a pale yellow solid.

TLC(in ethyl acetate:hexane=1:1); $R_f$=0.51
$^1$H-NMR(DMSO-$d_6$): δ11.20(s, 1H), 10.43(s, 1H), 9.07 (s, 1H), 7.93(m, 6H), 7.20(m,2H), 3.32(s, 3H), 2.44(s, 3H).

EXAMPLE 15

Preparation of N-[4-(N-hydroxycarbamoyl)phenyl]-N-methyl-[4-ethylphenyl]carboxyamide Except that methyl 4-[(4-ethylphenyl)carbonylamino] benzoate obtained in the intermediate step of Example 4 was used, the procedure described in Example 12 was performed to give the title compound (10.4 g, 42% yield) as a pale yellow solid.

TLC (in ethyl acetate:hexane=1:4); $R_f$=0.50
$^1$H-NMR(DMSO-$d_6$): δ11.20(s, 1H), 10.43(s, 1H), 9.05 (s, 1H), 7.91(m, 4H), 7.81(d, 2H, J=7.8 Hz), 7.50(d, 2H, J=7.8 Hz), 3.31(s, 3H), 2.51(m, 2H), 1.40(m, 3H).

EXAMPLE 16

Preparation of N-[4-N-hydroxycarbamoyl)phenyl]-N-methyl-[4-propylphenyl]carboxyamide Except that methyl 4-[(4-propylphenyl)carbonylamino] benzoate obtained in the intermediate step of Example 5 was used, the procedure described in Example 12 was performed to give the title compound (11.4 g, 43% yield) as a pale yellow solid.

TLC (in ethyl acetate:hexane=1:1); $R_f$=0.55
$^1$H-NMR(DMSO-$d_6$): δ11.23(s, 1H), 10.40(s, 1H), 9.03 (s, 1H), 7.92(m, 4H), 7.83(d, 1H, J=7.8 Hz), 7.48(d, 1H, J=7.8 Hz), 3.34(s, 3H), 2.50(m, 2H), 1.51(m, 2H), 0.95(m, 3H).

EXAMPLE 17

Preparation of N-[4-N-hydroxycarbamoyl)phenyl]-N-methyl-[4-isopropylphenyl]carboxyamide Except that methyl 4-[(4-isopropylphenyl)carbonylamino]benzoate obtained in the intermediate step of Example 6 was used, the procedure described in Example 12 was performed to give the title compound (10.1 g, 40% yield) as a pale yellow solid.

TLC (in ethyl acetate:hexane=1:1); $R_f$=0.50

$^1$H-NMR(DMSO-d$_6$): δ11.20(s, 1H), 10.41(s, 1H), 9.07 (s, 1H), 7.94(m, 4H), 7.80(d, 2H, J=7.8 Hz), 7.49(d, 2H, J=7.8 Hz), 3.35(s, 3H), 3.0(m, 1H), 1.30(d, 6H, J=6.9 Hz).

EXAMPLE 18

Preparation of N-[4-(N-hydroxycarbamoyl)phenyl]-N-methyl-[4-butylphenyl]carboxyamide Except that methyl 4-[(4-butylphenyl)carbonylamino] benzoate obtained in the intermediate step of Example 7 was used, the procedure described in Example 12 was performed to give the title compound (12.1 g, 47% yield) as a pale yellow solid.

TLC (in ethyl acetate:hexane=1:1); $R_f$=0.53

$^1$H-NMR(DMSO-d$_6$): 11.23(s, 1H), 10.41(s, 1H), 9.03(s, 1H), 7.92(m, 4H), 7.83(d, 2H, J=7.8 Hz), 7.53(d, 2H, J=7.8 Hz), 3.30(m, 3H), 2.49(m, 2H), 1.60(m, 2H), 1.41(m, 2H), 0.95(m, 3H).

EXAMPLE 19

Preparation of N-[4-(N-hydroxycarbamoyl)phenyl]-N-methyl-[4-tert-butylphenyl]carboxyamide Except that methyl 4-[(4-tert-butylphenyl)carbonylamino]benzoate obtained in the intermediate step of Example 8 was used, the procedure described in Example 12 was performed to give the title compound (11.1 g, 43% yield) as a pale yellow solid.

TLC (in ethyl acetate:hexane=1:1); $R_f$=0.51

$^1$H-NMR(DMSO-d$_6$): 11.21(s, 1H), 10.41(s, 1H), 9.05(s, 1H), 7.90(m, 4H), 7.79(d, 2H, J=7.8 Hz), 7.43(d, 2H, J=7.8 Hz), 3.32(s, 3H), 1.25(s, 9H).

EXAMPLE 20

Preparation of N-[4-(N-hydroxcarbamoly)phenyl]-N-methyl-[3,4-dimethylphenyl]carboxyamide Except that methyl 4-[(3,4-dimethylphenyl)carbonylamino]benzoate obtained in the intermediate step of Example 9 was used, the procedure described in Example 12 was performed to give the title compound (12.2 g, 44% yield) as a pale yellow solid.

TLC (in ethyl acetate:hexane=1:1); $R_f$=0.52

$^1$H-NMR(DMSO-d$_6$): δ11.25(s, 1H), 10.43(s, 1H), 9.07 (s, 1H), 7.94(m, 3H), 7.82(d, 2H, J=7.8 Hz), 7.49(d, 2H, J=7.8 Hz), 3.30(s, 3H), 2.48(s, 3H), 2.45(s, 3H).

EXAMPLE 21

Preparation of N-[4-(N-hydroxycarbamoyl)phenyl] adamantyl-N-methylcarboxyamide

Except that methyl 4-(adamantylcarbonylamino) benzoate obtained in the intermediate step of Example 10 was used, the procedure described in Example 12 was performed to give the title compound (12.8 g, 38% yield) as a pale yellow solid.

TLC (in ethyl acetate:hexane=1:1); $R_f$=0.53

$^1$H-NMR(DMSO-d$_6$): δ11.20(s, 1H), 9.23(s, 1H), 7.76(m, 4H), 3.74 (s, 3H), 1.96(m, 3H), 1.85(m, 6H), 1.64(m, 6H).

EXAMPLE 22

Preparation of adamantyl-N-[4-(N-hydroxy-N-methylcarbamoyl)phenyl]-N-methylcarboxyamide Except that N-methyl hydroxylamine hydrochloride was used instead of hydroxylamine hydrochloride, the procedure described in Example 21 was performed to give the title compound (11.4 g, 39% yield) as a pale yellow solid.

TLC(in ethyl acetate:hexane=1:4); $R_f$=0.54

$^1$H-NMR(DMSO-d$_6$): δ9.95(s, 1H), 7.57(m, 4H), 3.72(s, 3H), 3.07(s, 3H), 1.94(m, 3H), 1.87(m, 6H), 1.62(m, 6H).

EXAMPLE 23

Preparation of N-[4-(N-hydroxycarbamoylmethyl)phenyl]benzamide

Except that 4-aminophenylacetic acid methylester was used instead of methyl 4-aminobenzoate, the procedure described in Example 1 was performed to give the title compound (10.0 g, 39% yield) as a pale yellow solid.

TLC (in ethyl acetate:hexane=1:1); $R_f$=0.53

$^1$H-NMR(DMSO-d$_6$): δ11.23(s, 1H), 10.39(s, 1H), 9.04 (s, 1H), 8.01(m, 5H), 7.64(m, 4H), 3.20(s, 2H).

EXAMPLE 24

Preparation of N-[4-(N-hydroxycarbamoylmethyl) phenyl][4-methylphenyl]carboxyamide Except that 4-aminophenylacetic acid methylester was used instead of methyl 4-aminobenzoate, the procedure described in Example 2 was performed to give the title compound (11.9 g, 44% yield) as a pale yellow solid.

TLC (in ethyl acetate:hexane=1:1); $R_f$=0.52

$^1$H-NMR(DMSO-d$_6$): 11.22(s, 1H), 10.41(s, 1H), 9.07(s, 1H), 7.94(m, 4H), 7.80(d, 2H, J=7.8 Hz), 7.49(d, 2H, J=7.8 Hz), 3.21(s, 2H), 2.45(s, 3H).

EXAMPLE 25

Preparation of N-[4-(N-hydroxycarbamoylmethyl) phenyl][3-methylphenyl]carboxyamide Except that 4-aminophenylacetic acid methylester was used instead of methyl 4-aminobenzoate, the same procedure described in Example 3 was performed to give the title compound (11.9 g, 44% yield) as a pale yellow solid.

TLC (in ethyl acetate:hexane=1:1); $R_f$=0.54

$^1$H-NMR(DMSO-d$_6$): δ11.20(s, 1H), 10.40(s, 1H), 9.04 (s, 1H), 7.91(m, 6H), 7.22(m, 2H), 3.21(s, 2H), 2.44(s, 3H).

EXAMPLE 26

Preparation of N-[4-(N-hydroxycarbamoylmethyl) phenyl][4-ethylphenyl]carboxyamide Except that 4-aminophenylacetic acid methylester was used instead of methyl 4-aminobenzoate, the procedure described in Example 4 was performed to give the title compound (12.9 g, 45% yield) as a pale yellow solid.

TLC (in ethyl acetate:hexane=1:4); $R_f$=0.50

$^1$H-NMR(DMSO-d$_6$): δ11.20(s, 1H), 10.43(s, 1H), 9.05 (s, 1H), 7.91(m, 4H), 7.81(d, 2H, J=7.8 Hz), 7.50(d, 2H, J=7.8 Hz), 3.21(s, 2H), 2.51(m, 2H), 1.40(m, 3H).

EXAMPLE 27

Preparation of N-[4-(N-hydroxycarbamoylmethyl)phenyl][4-propylphenyl]carboxyamide Except that 4-aminophenylacetic acid methylester was used instead of methyl 4-aminobenzoate, the procedure described in Example 5 was performed to give the title compound (13.1 g, 46% yield) as a pale yellow solid.

TLC (in ethyl acetate:hexane=1:1); $R_f$=0.55
$^1$H-NMR(DMSO-$d_6$): δ11.23(s, 1H), 10.40(s, 1H), 9.03(s, 1H), 7.92(m, 4H), 7.83(d, 1H, J=7.8 Hz), 7.48(d, 1H, J=7.8 Hz), 3.20(s, 2H), 2.50(m, 2H), 1.51(m, 2H), 0.95(m, 3H).

EXAMPLE 28

Preparation of N-[4-(N-hydroxycarbamoylmethyl)phenyl][4-isopropylphenyl]carboxyamide Except that 4-aminophenylacetic acid methylester was used instead of methyl 4-aminobenzoate, the procedure described in Example 6 was performed to give the title compound (11.1 g, 43% yield) as a pale yellow solid.

TLC (in ethyl acetate:hexane=1:1); $R_f$=0.50
$^1$H-NMR(DMSO-$d_6$): δ11.20(s, 1H), 10.41(s, 1H), 9.05(s, 1H), 7.93(m, 4H), 7.81(d, 2H, J=7.8 Hz), 7.48(d, 2H, J=7.8 Hz), 3.23(s, 2H), 3.01(m, 1H), 1.30(d, 6H, J=6.9 Hz).

EXAMPLE 29

Preparation of N-[4-(N-hydroxycarbamoylmethyl)phenyl][4-butylphenyl]carboxyamide Except that 4-aminophenylacetic acid methylester was used instead of methyl 4-aminobenzoate, the procedure described in Example 7 was performed to give the title compound (11.9 g, 44% yield) as a pale yellow solid.

TLC (in ethyl acetate:hexane=1:1); $R_f$=0.53
$^1$H-NMR(DMSO-$d_6$): 11.22(s, 1H), 10.40(s, 1H), 9.07(s, 1H), 7.91(m, 4H), 7.83(d, 2H, J=7.8 Hz), 7.52(d, 2H, J=7.8 Hz), 3.19(s, 2H), 2.49(m, 2H), 1.60(m, 2H), 1.41(m, 2H), 0.95(m, 3H).

EXAMPLE 30

Preparation of N-[4-(N-hydroxycarbamoylmethyl)phenyl][4-tert-butylphenyl]carboxyamide Except that 4-aminophenylacetic acid methylester was used instead of methyl 4-aminobenzoate, the procedure described in Example 8 was performed to give the title compound (12.0 g, 42% yield) as a pale yellow solid.

TLC (in ethyl acetate:hexane=1:1); $R_f$=0.51
$^1$H-NMR(DMSO-$d_6$): 11.22(s, 1H), 10.41(s, 1H), 9.06(s, 1H), 7.91(m, 4H), 7.83(d, 2H, J=7.8 Hz), 7.52(d, 2H, J=7.8 Hz), 3.20(s, 2H), 1.25(s, 9H).

EXAMPLE 31

Preparation of N-[4-(N-hydroxycarbamoylmethyl)phenyl][3,4-dimethylphenyl]carboxyamide Except that 4-aminophenylacetic acid methylester was used instead of methyl 4-aminobenzoate, the procedure described in Example 9 was performed to give the title compound (11.9 g, 44% yield) as a pale yellow solid.

TLC (in ethyl acetate:hexane=1:1); $R_f$=0.52
$^1$H-NMR(DMSO-$d_6$): δ11.20(s, 1H), 10.41(s, 1H), 9.05(s, 1H), 7.92(m, 3H), 7.80(d, 2H, J=7.8 Hz), 7.47(d, 2H, J=7.8 Hz), 3.21(s, 2H), 2.48(s, 3H), 2.44(s, 3H).

EXAMPLE 32

Preparation of N-[4-(N-hydroxycarbamoylmethyl)phenyl]adamantyl carboxyamide

Except that 4-aminophenylacetic acid methylester was used instead of methyl 4-aminobenzoate, the procedure described in Example 10 was performed to give the title compound (11.9 g, 44% yield) as a pale yellow solid.

TLC (in ethyl acetate:hexane=1:1); $R_f$=0.52
$^1$H-NMR(DMSO-$d_6$): δ11.22(s, 1H), 9.25(s, 1H), 8.87(s, 1H), 7.76(m, 4H), 3.27(s, 2H), 1.96(m, 3H), 1.87(m, 6H), 1.63(m, 6H).

EXAMPLE 33

Preparation of 2-[4-(adamantlycarbonylamino)phenyl]-N-hydroxy-N-methylacetamide

Except that N-methyl hydroxylamine hydrochloride was used instead of hydroxylamine hydrochloride, the procedure described in Example 32 was performed to give the title compound (12.8 g, 41% yield) as a pale yellow solid.

TLC (in ethyl acetate:hexane=1:1); $R_f$=0.53
$^1$H-NMR(DMSO-$d_6$): δ9.95(s, 1H), 9.12(s, 1H), 7.55(m, 4H), 3.27(s, 2H), 3.09(s, 3H), 1.94(m, 3H), 1.84(m, 6H), 1.60(m, 6H).

EXAMPLE 34

Preparation of [4-(N-hydroxycarbamoyl)phenyl]-N-benzamide

Except that monomethylterephthalate and aniline were used instead of benzoic acid and methyl 4-aminobenzoate, the procedure described in Example 1 was performed to give the title compound (11.8 g, 46% yield) as a pale yellow solid.

TLC (in ethyl acetate:hexane=1:1); $R_f$=0.51
$^1$H-NMR(DMSO-$d_6$):δ11.21(s, 1H), 10.29(s, 1H), 9.10(s, 1H), 8.01(m, 4H), 7.60(m, 5H).

EXAMPLE 35

Preparation of [4-(N-hydroxycarbamoyl)phenyl]-N-[4-methylphenyl]carboxyamide

Except that monomethylterephthalate and 4-methylaniline were used instead of benzoic acid and methyl 4-aminobenzoate, the procedure described in Example 1 was performed to give the title compound (11.6 g, 43% yield) as a pale yellow solid.

TLC (in ethyl acetate:hexane=1:1); $R_f$=0.49
$^1$H-NMR(DMSO-$d_6$): δ11.20(s, 1H), 10.32(s, 1H), 9.11(s, 1H), 8.10(d, 2H, J=7.8 Hz), 7.98(d, 2H, J=7.8 Hz), 7.80(m, 4H), 2.44(s, 3H).

EXAMPLE 36

Preparation of [4-(N-hydroxycarbamoyl)phenyl]-N-[3-methylphenyl]carboxyamide

Except that monomethylterephthalate and 3-methylaniline were used instead of benzoic acid and methyl 4-aminobenzoate, the procedure described in Example 1 was performed to give the title compound (11.6 g, 43% yield) as a pale yellow solid.

TLC (in ethyl acetate:hexane=1:1); $R_f$=0.49
$^1$H-NMR(DMSO-$d_6$): δ11.20(s, 1H), 10.32(s, 1H), 9.10 (s, 1H), 8.10(m, 6H), 7.90(m, 2H), 2.42(s, 3H).

EXAMPLE 37

Preparation of [4-(N-hydroxycarbamoyl)phenyl]-N-[4-ethylphenyl]carboxyamide

Except that monomethylterephthalate and 4-ethylaniline were used instead of benzoic acid and methyl 4-aminobenzoate, the procedure described in Example 1 was performed to give the title compound (12.8 g, 45% yield) as a pale yellow solid.

TLC (in ethyl acetate:hexane=1:1); $R_f$=0.51
$^1$H-NMR(DMSO-$d_6$): δ11.20(s, 1H), 10.33(s, 1H), 9.09 (s, 1H), 8.12(d, 2H, J=7.8 Hz), 7.97(d, 2H, J=7.8 Hz), 7.81(m, 4H), 2.53(m, 2H), 1.42(m, 3H).

EXAMPLE 38

Preparation of [4-(N-hydroxycarbamoyl)phenyl]-N-[4-propylphenyl]carboxyamide

Except that monomethylterephthalate and 4-propylaniline were used instead of benzoic acid and methyl 4-aminobenzoate, the procedure described in Example 1 was performed to give the title compound (11.6 g, 39% yield) as a pale yellow solid.

TLC (in ethyl acetate:hexane=1:1); $R_f$=0.53
$^1$H-NMR(DMSO-$d_6$): δ11.22(s, 1H), 10.33(s, 1H), 9.10 (s, 1H), 8.13(d, 2H, J=7.8 Hz), 7.96(d, 2H, J=7.8 Hz), 7.88(m, 4H), 2.46(m, 2H), 1.50(m, 2H), 0.98(m, 3H).

EXAMPLE 39

Preparation of [4-(N-hydroxycarbamoyl)phenyl]-N-[4-isopropylphenyl]carboxyamide

Except that monomethylterephthalate and 4-isopropylaniline were used instead of benzoic acid and methyl 4-aminobenzoate, the procedure described in Example 1 was performed to give the title compound (12.2 g, 41% yield) as a pale yellow solid.

TLC (in ethyl acetate:hexane=1:1); $R_f$=0.51
$^1$H-NMR (DMSO-$d_6$): 11.20(s, 1H), 10.31(s, 1H), 9.11(s, 1H), 8.11(d, 2H, J=7.8 Hz), 7.99(d, 2H, J=7.8 Hz), 7.81(m, 4H), 2.99(m, 1H), 1.30(d, 6H, J=6.9 Hz).

EXAMPLE 40

Preparation of [4-(N-hydroxycarbamoyl)phenyl]-N-[4-butylphenyl]carboxyamide

Except that monomethylterephthalate and 4-butylaniline were used instead of benzoic acid and methyl 4-aminobenzoate, the procedure described in Example 1 was performed to give the title compound (12.8 g, 41% yield) as a pale yellow solid.

TLC (in ethyl acetate:hexane=1:1); $R_f$=0.51
$^1$H NMR (DMSO-$d_6$): δ11.21(s, 1H), 10.33(s, 1H), 9.13 (s, 1H), 8.13(d, 2H, J=7.8 Hz), 7.95(d, 2H, J=7.8 Hz), 7.88(m, 4H), 2.50(m, 2H), 2.00(m, 2H), 1.48(m, 2H), 0.95 (m, 3H).

EXAMPLE 41

Preparation of [4-(N-hydroxycarbamoyl)phenyl]-N-[4-tert-butylphenyl]carboxyamide Except that monomethylterephthalate and 4-tert-butylaniline were used instead of benzoic acid and methyl 4-aminobenzoate, the procedure described in Example 1 was performed to give the title compound (12.8 g, 41% yield) as a pale yellow solid.

TLC (in ethyl acetate:hexane=1:1); $R_f$=0.51
$^1$H-NMR(DMSO-$d_6$): δ11.21(s, 1H), 10.31(s, 1H), 9.10 (s, 1H), 8.15(d, 2H, J=7.8 Hz), 7.94(d, 2H, J=7.8 Hz), 7.85(m, 4H), 1.40(s, 9H).

EXAMPLE 42

Preparation of [4-(N-hydroxycarbamoyl)phenyl]-N-[3,4-dimethylphenyl]carboxyamide Except that monomethylterephthalate and 3,4-dimethylaniline were used instead of benzoic acid and methyl 4-aminobenzoate, the procedure described in Example 1 was performed to give the title compound (11.6 g, 43% yield) as a pale yellow solid.

TLC (in ethyl acetate:hexane=1:1); $R_f$=0.49
$^1$H-NMR (DMSO-$d_6$): δ11.20(s, 1H), 10.30(s, 1H), 9.11 (s, 1H), 8.10(d, 2H, J=7.8 Hz), 7.98(d, 2H, J=7.8 Hz), 7.84(m, 3H), 2.46(s, 3H), 2.42(s, 3H).

EXAMPLE 43

Preparation of [4-(N-hydroxycarbamoyl)phenyl]-N-adamantyl carboxyamide

Except that monomethylterephthalate and adamantamine were used instead of adamantanecarboxylic acid and methyl 4-aminobenzoate, the procedure described in Example 10 was performed to give the title compound (11.8 g, 46% yield) as a pale yellow solid.

TLC (in ethyl acetate:hexane=1:1); $R_f$=0.51
$^1$H-NMR (DMSO-$d_6$): δ11.20(s, 1H), 9.21(s, 1H), 8.87(s, 1H), 7.73(m, 4H), 1.94(m, 3H), 1.84(m, 6H), 1.62(m, 6H).

EXAMPLE 44

Preparation of N-adamantyl [4-(N-hydroxy-N-methylcarbamoyl)phenyl]carboxyamide

Except that N-methyl hydroxylamine hydrochloride was used instead of hydroxylamine hydrochloride, the procedure described in Example 43 was performed to give the title compound (11.8 g, 46% yield) as a pale yellow solid.

TLC (in ethyl acetate:hexane=1:1); $R_f$=0.51
$^1$H-NMR(DMSO-$d_6$): δ9.99(s, 1H), 9.10(s, 1H), 7.53(m, 4H), 3.10(s, 3H), 1.91(m, 3H), 1.83(m, 6H), 1.60(m, 6H).

EXAMPLE 45

Preparation of [4-(N-hydroxycarbamoyl)phenyl]-N-methyl-N-benzamide

Except that methyl 4-(phenylcarbamoyl) benzoate obtained in the intermediate step of Example 34 was used, the procedure described in Example 12 was performed to give the title compound (12.0 g, 40% yield) as a pale yellow solid.

TLC (in ethyl acetate:hexane=1:1); $R_f$=0.51
$^1$H-NMR(DMSO-d$_6$): δ11.21(s, 1H), 10.29(s, 1H), 9.10 (s, 1H), 8.01(m, 4H), 7.60(m, 5H), 3.20(s, 3H).

EXAMPLE 46

Preparation of [4-(N-hydroxycarbamoyl)phenyl]-N-methyl-N-[4-methylphenyl]carboxyamide Except that methyl 4-[(4-methylphenyl)carbamoyl]benzoate obtained in the intermediate step of Example 35 was used, the procedure described in Example 12 was performed to give the title compound (11.0 g, 39% yield) as a pale yellow solid.

TLC (in ethyl acetate:hexane=1:1); $R_f$=0.51
$^1$H-NMR(DMSO-d$_6$): δ11.20(s, 1H), 10.39(s, 1H), 9.11(s, 1H), 8.11(d, 2H, J=7.8 Hz), 7.98(d, 2H, J=7.8 Hz), 7.91(m, 4H), 3.20(s, 3H), 2.50(s, 3H).

EXAMPLE 47

Preparation of [4-(N-hydroxycarbamoyl)phenyl]-N-methyl-N-[3-methylphenyl]carboxyamide Except that methyl 4-[(3-methylphenyl)carbamoyl]benzoate obtained in the intermediate step of Example 36 was used, the procedure described in Example 12 was performed to give the title compound (11.0 g, 39% yield) as a pale yellow solid.

TLC (in ethyl acetate:hexane=1:1); $R_f$=0.51
$^1$H-NMR(DMSO-d$_6$): δ11.21(s, 1H), 10.30(s, 1H), 9.13 (s, 1H), 8.10(m, 6H), 7.88(m, 2H), 2.50(s, 3H).

EXAMPLE 48

Preparation of [4-(N-hydroxycarbamoyl)phenyl]-N-methyl-N-[4-ethylphenyl]carboxyamide Except that methyl 4-[(4-ethylphenyl)carbamoyl]benzoate obtained in the intermediate step of Example 37 was used, the procedure described in Example 12 was performed to give the title compound (12.0 g, 40% yield) as a pale yellow solid.

TLC (in ethyl acetate:hexane=1:1); $R_f$=0.55
$^1$H-NMR(DMSO-d$_6$): δ11.22(s, 1H), 10.33(s, 1H), 9.10 (s, 1H), 8.13(d, 2H, J=7.8 Hz), 7.97(d, 2H, J=7.8 Hz), 7.89(m, 4H), 3.20(s, 3H), 2.46(m, 2H), 0.98(m, 3H).

EXAMPLE 49

Preparation of [4-(N-hydroxycarbamoyl)phenyl]-N-methyl-N-[4-propylphenyl]carboxyamide Except that methyl 4-[(4-propylphenyl)carbamoyl]benzoate obtained in the intermediate step of Example 38 was used, the procedure described in Example 12 was performed to give the title compound (12.8 g, 41% yield) as a pale yellow solid.

TLC (in ethyl acetate:hexane=1:1); $R_f$=0.55
$^1$H-NMR(DMSO-d$_6$): δ11.20(s, 1H), 10.31(s, 1H), 9.13 (s, 1H), 8.12(d, 2H, J=7.8 Hz), 7.96(d, 2H, J=7.8 Hz), 7.89(m, 4H), 3.20(s, 3H), 2.46(m, 2H), 1.50(m, 2H), 0.98(m, 3H).

EXAMPLE 50

Preparation of [4-(N-hydroxycarbamoyl)phenyl]-N-methyl-N-[4-isopropylphenyl]carboxyamide Except that methyl 4-[(4-isopropylphenyl)carbamoyl]benzoate obtained in the intermediate step of Example 39 was used, the procedure described in Example 12 was performed to give the title compound (13.2 g, 44% yield) as a pale yellow solid.

TLC (in ethyl acetate:hexane=1:1); $R_f$=0.51
$^1$H-NMR(DMSO-d$_6$): δ11.21(s, 1H), 10.32(s, 1H), 9.15 (s, 1H), 8.10(d, 2H, J=7.8 Hz), 7.94(d, 2H, J=7.8 Hz), 7.83(m, 4H), 3.21(s, 3H), 2.50(m, 1H), 1.32(d, 6H, J=6.9 Hz).

EXAMPLE 51

Preparation of [4-(N-hydroxycarbamoyl)phenyl]-N-methyl-N-[4-butylphenyl]carboxyamide Except that methyl 4-[(4-butylphenyl)carbamoyl]benzoate obtained in the intermediate step of Example 40 was used, the procedure described in Example 12 was performed to give the title compound (12.0 g, 40% yield) as a pale yellow solid.

TLC (in ethyl acetate:hexane=1:1); $R_f$=0.51
$^1$H-NMR(DMSO-d$_6$): δ11.20(s, 1H), 10.33(s, 1H), 9.14 (s, 1H), 8.12(d, 2H, J=7.8 Hz), 7.95(d, 2H, J=7.8 Hz), 7.84(m, 4H), 3.22(s, 3H), 2.50(m, 2H), 2.00(m, 2H), 1.48(m, 2H), 0.95(m, 3H).

EXAMPLE 52

Preparation of [4-(N-hydroxycarbamoyl)phenyl]-N-methyl-N-[4-tert-butylphenyl]carboxamide Except that methyl 4-[(4-tert-butylphenyl)carbamoyl]benzoate obtained in the intermediate step of Example 41 was used, the procedure described in Example 12 was performed to give the title compound (12.5 g, 41% yield) as a pale yellow solid.

TLC (in ethyl acetate:hexane=1:1); $R_f$=0.51
$^1$H-NMR(DMSO-d$_6$): δ11.22(s, 1H), 10.33(s, 1H), 9.12 (s, 1H), 8.11(d, 2H, J=7.8 Hz), 7.96(d, 2H, J=7.8 Hz), 7.84(m, 4H), 3.20(s, 3H), 1.24(s, 9H).

EXAMPLE 53

Preparation of [4-(N-hydroxycarbamoyl)phenyl]-N-methyl-N-[3,4-dimethylphenyl]carboxyamide Except that methyl 4-[(3,4-dimethylphenyl)carbamoyl]benzoate obtained in the intermediate step of Example 42 was used, the procedure described in Example 12 was performed to give the title compound (11.0 g, 39% yield) as a pale yellow solid.

TLC (in ethyl acetate:hexane=1:1); $R_f$=0.51
$^1$H-NMR(DMSO-4): δ11.20(s, 1H), 10.30(s, 1H), 9.11(s, 1H), 8.11(d, 2H, J=7.8 Hz), 7.95(d, 2H, J=7.8 Hz), 7.94(m, 3H), 3.20(s, 3H), 2.53(s, 3H), 2.50(s, 3H).

EXAMPLE 54

Preparation of [4-(N-hydroxycarbamoyl)phenyl]-N-adamantyl-N-methylcarboxyamide

Except that methyl 4-(N-adamantyl-N-methylcarbamoyl)benzoate obtained in the intermediate step of Example 43 was used, the procedure described in Example 12 was performed to give the title compound (11.8 g, 46% yield) as a pale yellow solid.

TLC (in ethyl acetate:hexane=1:1); $R_f$=0.51
$^1$H-NMR(DMSO-$d_6$): δ11.22(s, 1H), 9.22(s, 1H), 7.74(m, 4H), 3.71 (s, 3H), 1.93(m, 3H), 1.83(m, 6H), 1.63(m, 6H).

EXAMPLE 55

Preparation of N-adamantyl [4-(N-hydroxy-N-methylcarbamoyl)phenyl]-N-methyl carboxyamide Except that N-methyl hydroxylamine hydrochloride was used instead of hydroxylamine hydrochloride, the procedure described in Example 54 was performed to give the title compound (11.8 g, 46% yield) as a pale yellow solid.

TLC (in ethyl acetate:hexane=1:1); $R_f$=0.51
$^1$H-NMR(DMSO-$d_6$): δ9.93(s, 1H), 7.59(m, 4H), 3.70(s, 3H), 3.05(s, 3H), 1.92(m, 3H), 1.86(m, 6H), 1.60(m, 6H).

EXPERIMENTAL EXAMPLE 1

Affinity to Retinoic Acid Receptor

This example illustrates affinities of hydroxamic acid derivatives obtained in Examples 1 to 55 to retinoic acid receptor, in comparison with retinol and retinoic acid.

Receptor-expression plasmid, pECE-RARα and pECE-RARγ were engineered by the prior method (*Mol. Cell. Biol.* 1996, 16, 1138-1149). RARE-tk-Luc, i.e. RARE reporter was obtained by inserting RARE fragment from b-RARE-tk-CAT into pGL3 luciferase basic vector. CV-1 cells were obtained from ATCC (American Type Culture Collection).

CV-1 cells were seeded into 96-well microtiter plate at 5,000 cells per well and cultured in DMEM (Dulbecco's Modified Eagle's Media) supplemented with 2.5% fetal bovine serum. 24 Hours later, the cells were transfected with 10 ng of pECE-RARα, long of pECE-RARγ, 100 ng of reporter plasmid and 100 ng of β-galactosidase-expression vector, using LipofectaminPlus (GIBCO BRL, grand island, N.Y.). 24 Hours post-transfection, the cells were treated for 24 hours with hydroxamic acid derivatives of Examples 1~55 or retinol at a final concentration of $10^{-4}$M or with retinoic acid at a final concentration of $10^{-5}$M, which is 10 times lower concentration than those of the former.

TABLE 1

| Materials | Luciferase activity RARα | Luciferase activity RARγ |
|---|---|---|
| Control group (without | 1000 | 5000 |
| Retinol | 2500 | 6000 |
| Retinoic acid | 25000 | 10000 |
| Example 1 | 10000 | 12000 |
| Example 2 | 12000 | 11200 |
| Example 3 | 11600 | 10000 |
| Example 4 | 12000 | 12300 |
| Example 5 | 18000 | 11000 |
| Example 6 | 14500 | 12300 |
| Example 7 | 12000 | 11700 |
| Example 8 | 10002 | 12000 |
| Example 9 | 12000 | 12000 |
| Example 10 | 11000 | 12000 |
| Example 11 | 11600 | 10000 |
| Example 12 | 14500 | 11300 |
| Example 13 | 12000 | 11200 |
| Example 14 | 18000 | 10300 |
| Example 15 | 14500 | 10400 |
| Example 16 | 12300 | 11200 |
| Example 17 | 12400 | 11700 |
| Example 18 | 12900 | 11400 |
| Example 19 | 10020 | 11200 |
| Example 20 | 12200 | 12300 |
| Example 21 | 12500 | 11200 |
| Example 22 | 12100 | 12400 |
| Example 23 | 13000 | 13200 |
| Example 24 | 12100 | 11210 |
| Example 25 | 13200 | 12100 |
| Example 26 | 17500 | 11200 |
| Example 27 | 13920 | 11300 |
| Example 28 | 12900 | 10700 |
| Example 29 | 18900 | 10600 |
| Example 30 | 23500 | 12000 |
| Example 31 | 23100 | 10700 |
| Example 32 | 18000 | 10000 |
| Example 33 | 13400 | 11000 |
| Example 34 | 13900 | 11000 |
| Example 35 | 14500 | 11300 |
| Example 36 | 16700 | 11200 |
| Example 37 | 19000 | 10300 |
| Example 38 | 17500 | 10400 |
| Example 39 | 18700 | 10100 |
| Example 40 | 14300 | 11200 |
| Example 41 | 14300 | 11211 |
| Example 42 | 14500 | 11200 |
| Example 43 | 18900 | 10600 |
| Example 44 | 23100 | 10700 |
| Example 45 | 12300 | 11212 |
| Example 46 | 13200 | 11123 |
| Example 47 | 12200 | 11700 |
| Example 48 | 15500 | 11200 |
| Example 49 | 14500 | 12100 |
| Example 50 | 12300 | 11212 |
| Example 51 | 13400 | 12210 |
| Example 52 | 12400 | 12130 |
| Example 53 | 14500 | 12300 |
| Example 54 | 22500 | 11000 |
| Example 55 | 13400 | 11000 |

The above results for affinity to retinoic acid receptor indicate that hydroxamic acid derivatives obtained in Examples 1 to 55 can be regarded as retinoid compounds.

EXPERIMENTAL EXAMPLE 2

Effect on Collagen Biosynthesis

This example illustrates effects of hydroxamic acid derivatives obtained in Examples 1 to 55 on collagen biosynthesis, in comparison with retinol and retinoic acid.

Human fibroblasts were seeded into 24-well plate at $1 \times 10^5$ cells per well and then cultured to 90% of growth. Then, the fibroblastes were cultured in serum-free DMEM for 24 hours and treated with $10^{-4}$M of hydroxamic acid derivatives of Examples 1~55, retinol or retinoic acid in serum-free medium, and then incubated in $CO_2$ incubator for 24 hours.

For each supernatant, procollagen production was measured with procollagen type I ELISA kit. The results are shown in Table 2 and collagen biosynthesis was evaluated as a relative value, in consideration that the value of control group with no material treated is 100.

TABLE 2

| Materials | Collagen biosynthesis (%) |
|---|---|
| Control group | 100 |
| Retinol | 120 |
| Retinoic acid | 125 |
| Example 1 | 105 |
| Example 2 | 118 |
| Example 3 | 120 |
| Example 4 | 119 |
| Example 5 | 125 |
| Example 6 | 124 |
| Example 7 | 109 |
| Example 8 | 112 |
| Example 9 | 120 |
| Example 10 | 106 |
| Example 11 | 110 |
| Example 12 | 122 |
| Example 13 | 117 |
| Example 14 | 115 |
| Example 15 | 112 |
| Example 16 | 120 |
| Example 17 | 111 |
| Example 18 | 130 |
| Example 19 | 120 |
| Example 20 | 122 |
| Example 21 | 118 |
| Example 22 | 120 |
| Example 23 | 131 |
| Example 24 | 121 |
| Example 25 | 120 |
| Example 26 | 123 |
| Example 27 | 112 |
| Example 28 | 121 |
| Example 29 | 132 |
| Example 30 | 121 |
| Example 31 | 109 |
| Example 32 | 125 |
| Example 33 | 112 |
| Example 34 | 108 |
| Example 35 | 111 |
| Example 36 | 121 |
| Example 37 | 121 |
| Example 38 | 109 |
| Example 39 | 105 |
| Example 40 | 108 |
| Example 41 | 115 |
| Example 42 | 116 |
| Example 43 | 130 |
| Example 44 | 107 |
| Example 45 | 108 |
| Example 46 | 121 |
| Example 47 | 112 |
| Example 48 | 107 |
| Example 49 | 109 |
| Example 50 | 110 |
| Example 51 | 121 |
| Example 52 | 127 |
| Example 53 | 122 |
| Example 54 | 121 |
| Example 55 | 108 |

EXPERIMENTAL EXAMPLE 3

Inhibition of Collagenase Expression

This example illustrates inhibition by hydroxamic acid derivatives obtained in Examples 1 to 55 of collagenase expression, in comparison with retinol and retinoic acid.

Human fibroblasts were seeded into 96-well microtiter plate at 5,000 cells per well and then cultured to 90% of growth in DMEM (Dulbecco's Modified Eagle's Media) supplemented with 2.5% fetal bovine serum. Then, the fibroblastes were cultured in serum-free DMEM for 24 hours and treated for 24 hours with $10^{-4}$M of hydroxamic acid derivatives of Examples 1~55, retinol or retinoic acid in serum-free medium, and then the culture fluid was collected.

For each culture fluid, collagenase production was measured with collagenase kit (commercialized by Amersham-Pharmacia Biotech). Firstly, the culture fluid was added to 96-well plate spread with primary collagenase antibody and then antigen-antibody reaction was performed in an incubator for 3 hours. Later, chromophore-conjugated secondary antibody was added to the 96-well plate and then reacted for 15 minutes. Then, color former was added thereto, to induce development at room temperature for 15 minutes. 1M of sulfuric acid was added to stop the reaction. The reaction solution got yellow. The color density depends on the progress of the reaction. The absorbance of the yellow 96-well plate was measured at 405 nm using absorptiometer. Collagenase expression was calculated by the following equation 1. Herein, the absorbance of the culture fluid collected from the medium with no material treated was used as a control.

Collagenase expression (%)=(Absorbance of test group with said material treated/Absorbance of control group with no material treated)×100  [Equation 1]

The results for inhibition of collagenase expression in the cells are shown in Table 3 and confirmed that hydroxamic acid derivatives of the present invention could inhibit collagenase expression in vitro. Collagenase expression was evaluated as a relative value, in consideration that the value of control group with no material treated is 100.

TABLE 3

| Materials | Collagenase expression (%) |
|---|---|
| Control group | 100 |
| Retinol | 85 |
| Retinoic acid | 60 |
| Example 1 | 78 |
| Example 2 | 68 |
| Example 3 | 80 |
| Example 4 | 78 |
| Example 5 | 79 |
| Example 6 | 85 |
| Example 7 | 84 |
| Example 8 | 90 |
| Example 9 | 65 |
| Example 10 | 75 |
| Example 11 | 81 |
| Example 12 | 64 |
| Example 13 | 70 |
| Example 14 | 72 |
| Example 15 | 79 |
| Example 16 | 80 |
| Example 17 | 81 |
| Example 18 | 78 |
| Example 19 | 70 |
| Example 20 | 68 |
| Example 21 | 69 |
| Example 22 | 77 |
| Example 23 | 77 |
| Example 24 | 76 |
| Example 25 | 70 |
| Example 26 | 78 |
| Example 27 | 87 |
| Example 28 | 67 |
| Example 29 | 77 |
| Example 30 | 83 |
| Example 31 | 81 |
| Example 32 | 79 |
| Example 33 | 70 |

TABLE 3-continued

| Materials | Collagenase expression (%) |
|---|---|
| Example 34 | 85 |
| Example 35 | 90 |
| Example 36 | 68 |
| Example 37 | 70 |
| Example 38 | 87 |
| Example 39 | 78 |
| Example 40 | 77 |
| Example 41 | 88 |
| Example 42 | 78 |
| Example 43 | 77 |
| Example 44 | 83 |
| Example 45 | 81 |
| Example 46 | 83 |
| Example 47 | 79 |
| Example 48 | 87 |
| Example 49 | 81 |
| Example 50 | 80 |
| Example 51 | 76 |
| Example 52 | 77 |
| Example 53 | 75 |
| Example 54 | 83 |
| Example 55 | 85 |

EXPERIMENTAL EXAMPLE 4

Inhibition of Elastase Expression

This example illustrates inhibition by hydroxamic acid derivatives obtained in Examples 1 to 55 of elastase expression, in comparison with retinol and retinoic acid.

Human fibroblasts were seeded into 96-well microtiter plate at 5,000 cells per well and then cultured to 90% of growth in DMEM (Dulbecco's Modified Eagle's Media) supplemented with 2.5% fetal bovine serum. Then, the fibroblastes were cultured in serum-free DMEM for 24 hours and treated for 24 hours with $10^{-4}$M of hydroxamic acid derivatives of Examples 1~55, retinol or retinoic acid in serum-free medium, and then the culture fluid was collected.

For each culture fluid, elastase production was measured with elastase kit (commercialized by AmershamPharmacia Biotech). Firstly, the culture fluid was added to 96-well plate spread with primary elastase antibody and then antigen-antibody reaction was performed in an incubator for 3 hours. Later, chromophore-conjugated secondary antibody was added to the 96-well plate and then reacted for 15 minutes. Then, color former was added thereto, to induce development at room temperature for 15 minutes. 1M of sulfuric acid was added to stop the reaction. The reaction solution got yellow. The color density depends on the progress of the reaction. The absorbance of the yellow 96-well plate was measured at 405 nm using absorptiometer. Elastase expression was calculated by the following equation 2. Herein, the absorbance of the culture fluid collected from the medium with no material treated was used as a control.

Elastase expression (%)=(Absorbance of test group with said material treated/Absorbance of control group with no material treated)×100 [Equation 2]

The results for inhibition of elastase expression in the cells are shown in Table 4 and confirmed that hydroxamic acid derivatives of the present invention could inhibit elastase expression in vitro. Elastase expression was evaluated as a relative value, in consideration that the value of control group with no material treated is 100.

TABLE 4

| Materials | Elastase expression (%) |
|---|---|
| Control group | 100 |
| Retinol | 88 |
| Retinoic acid | 68 |
| Example 1 | 79 |
| Example 2 | 78 |
| Example 3 | 69 |
| Example 4 | 70 |
| Example 5 | 78 |
| Example 6 | 79 |
| Example 7 | 77 |
| Example 8 | 69 |
| Example 9 | 67 |
| Example 10 | 77 |
| Example 11 | 65 |
| Example 12 | 80 |
| Example 13 | 84 |
| Example 14 | 75 |
| Example 15 | 76 |
| Example 16 | 77 |
| Example 17 | 82 |
| Example 18 | 79 |
| Example 19 | 80 |
| Example 20 | 78 |
| Example 21 | 78 |
| Example 22 | 70 |
| Example 23 | 79 |
| Example 24 | 82 |
| Example 25 | 80 |
| Example 26 | 86 |
| Example 27 | 87 |
| Example 28 | 79 |
| Example 29 | 70 |
| Example 30 | 69 |
| Example 31 | 63 |
| Example 32 | 74 |
| Example 33 | 82 |
| Example 34 | 70 |
| Example 35 | 71 |
| Example 36 | 79 |
| Example 37 | 80 |
| Example 38 | 69 |
| Example 39 | 87 |
| Example 40 | 90 |
| Example 41 | 78 |
| Example 42 | 76 |
| Example 43 | 70 |
| Example 44 | 63 |
| Example 45 | 81 |
| Example 46 | 80 |
| Example 47 | 83 |
| Example 48 | 87 |
| Example 49 | 87 |
| Example 50 | 78 |
| Example 51 | 77 |
| Example 52 | 87 |
| Example 53 | 80 |
| Example 54 | 67 |
| Example 55 | 70 |

EXPERIMENTAL EXAMPLE 5

Primary Skin Irritation Test on Animals

1) Method

Test was performed using fifty-six (56) of healthy male rabbits whose backs were depilated. The compounds of Examples 1~55 were dissolved in solvent (1,3-butylene glycol: ethanol 7:3) to give 1% solution of test samples. 0.5ml of the test sample solution was applied to the right site of 2.5 cm×2.5 cm region on each of the depilated back. Left site with no sample treated was compared as a control. 24 hours or 72 hours later, skin abnormality such as erythema, crust and edema was observed. Skin response was scored according to "standard guide for toxicity test of foods and drugs", as shown in Table 5.

Based on the score of skin response, skin irritation was evaluated according to Draize's P.I.I.(Primary Irritation Index) and compared with retinoic acid. The results are shown in Table 6.

TABLE 5

| | Skin responses | Score |
|---|---|---|
| 1) Erythema and crust | No erythema | 0 |
| | A slight erythema (scarcely visible) | 1 |
| | Significant erythema | 2 |
| | Severe erythema | 3 |
| | Crimson extremely-severe erythema and crust | 4 |
| 2) Edema | No edema | 0 |
| | A slight edema (scarcely visible) | 1 |
| | Significant edema (distinct from periphery) | 2 |
| | Severe edema (swelled up about 1 mm) | 3 |
| | Extremely-severe edema (swelled up 1 mm or more and expanded out of the exposed site) | 4 |

TABLE 6

| Materials | P.I.I. | Evaluation |
|---|---|---|
| Retinoic acid | 1.830 | Light irritation |
| Example 1 | 0.375 | No irritation |
| Example 2 | 0.345 | No irritation |
| Example 3 | 0.375 | No irritation |
| Example 4 | 0.350 | No irritation |
| Example 5 | 0.375 | No irritation |
| Example 6 | 0.315 | No irritation |
| Example 7 | 0.312 | No irritation |
| Example 8 | 0.330 | No irritation |
| Example 9 | 0.470 | No irritation |
| Example 10 | 0.375 | No irritation |
| Example 11 | 0.375 | No irritation |
| Example 12 | 0.410 | No irritation |
| Example 13 | 0.500 | No irritation |
| Example 14 | 0.231 | No irritation |
| Example 15 | 0.789 | No irritation |
| Example 16 | 0.567 | No irritation |
| Example 17 | 0.123 | No irritation |
| Example 18 | 0.321 | No irritation |
| Example 19 | 0.223 | No irritation |
| Example 20 | 0.421 | No irritation |
| Example 21 | 0.345 | No irritation |
| Example 22 | 0.350 | No irritation |
| Example 23 | 0.321 | No irritation |
| Example 24 | 0.321 | No irritation |
| Example 25 | 0.423 | No irritation |
| Example 26 | 0.321 | No irritation |
| Example 27 | 0.568 | No irritation |
| Example 28 | 0.765 | No irritation |
| Example 29 | 0.234 | No irritation |
| Example 30 | 0.456 | No irritation |
| Example 31 | 0.567 | No irritation |
| Example 32 | 0.375 | No irritation |
| Example 33 | 0.765 | No irritation |
| Example 34 | 0.678 | No irritation |
| Example 35 | 0.245 | No irritation |
| Example 36 | 0.456 | No irritation |
| Example 37 | 0.456 | No irritation |
| Example 38 | 0.567 | No irritation |
| Example 39 | 0.145 | No irritation |
| Example 40 | 0.546 | No irritation |
| Example 41 | 0.367 | No irritation |
| Example 42 | 0.987 | No irritation |
| Example 43 | 0.456 | No irritation |
| Example 44 | 0.678 | No irritation |
| Example 45 | 0.900 | No irritation |
| Example 46 | 0.345 | No irritation |
| Example 47 | 0.367 | No irritation |
| Example 48 | 0.468 | No irritation |
| Example 49 | 0.342 | No irritation |
| Example 50 | 0.234 | No irritation |
| Example 51 | 0.331 | No irritation |
| Example 52 | 0.412 | No irritation |
| Example 53 | 0.321 | No irritation |
| Example 54 | 0.567 | No irritation |
| Example 55 | 0.245 | No irritation |

As shown in Table 6, hydroxamic acid derivatives obtained in Examples 1 to 55 were confirmed to be non-irritative to the skin.

These results illustrate that hydroxamic acid derivatives of the present invention have the same efficacy in improving skin elasticity as that of retinol or retinoic acid, and additionally good safety and less skin irritation, to be incorporated into skin-care external compositions for improving skin elasticity.

EXPERIMENTAL EXAMPLE 6

Phototoxicity Test

Test was performed for twenty-five (25) of white guinea pigs whose backs were depilated and fixed. On both sides of the back, six(6) sites of 2 cm×2 cm, three(3) per side were sectioned. Right sites were compared as controls with no irradiation (UV non-irradiation sites) and left sites were irradiated (UV irradiation sites). As a negative control, vehicle of 1,3-butylene glycol:ethanol=7:3 and as a positive control, 0.1% 8-MOP(methoxypsoralene) were prepared, and then hydroxamic acid derivatives of Examples 1~55 were dissolved in 1,3-butylene glycol:ethanol=7:3, to give 1%(w/v) of solutions, of which each 50 μl was applied.

30 Minutes later, right sites were shielded with aluminum foil and UVA(320~380 nm) was irradiated at a distance of about 10 cm therefrom using Waldmann to the final energy of 15 J/cm². After 24, 48 and 72 hours elapsed, skin response of guinea pig was observed. Erythema and edema were scored from 0 to 4, as shown in said Table 5 and skin response was evaluated by the sum of scores. Evaluation was estimated for each elapsed time, i.e. 24, 48 and 72 hours and maximum scores were selected, to calculate irritation index by the following equation 3. Then, phototoxic index was calculated by the following equation 4. The results are shown in Table 7.

Irritation index=(ΣMaximum of erythema+ΣMaximum of edema)/Number of animals  [Equation 3]

Phototoxic index=(Irritation index of UV irradiation site)−(Irritation index of UV non-irradiation site)  Equation 4]

TABLE 7

| Materials | Phototoxic index | Evaluation |
|---|---|---|
| Example 1 | 0 | No phototoxicity |
| Example 2 | 0 | No phototoxicity |
| Example 3 | 0 | No phototoxicity |
| Example 4 | 0 | No phototoxicity |
| Example 5 | 0 | No phototoxicity |
| Example 6 | 0 | No phototoxicity |
| Example 7 | 0 | No phototoxicity |
| Example 8 | 0 | No phototoxicity |
| Example 9 | 0 | No phototoxicity |

TABLE 7-continued

| Materials | Phototoxic index | Evaluation |
|---|---|---|
| Example 10 | 0 | No phototoxicity |
| Example 11 | 0 | No phototoxicity |
| Example 12 | 0 | No phototoxicity |
| Example 13 | 0 | No phototoxicity |
| Example 14 | 0 | No phototoxicity |
| Example 15 | 0 | No phototoxicity |
| Example 16 | 0 | No phototoxicity |
| Example 17 | 0 | No phototoxicity |
| Example 18 | 0 | No phototoxicity |
| Example 19 | 0 | No phototoxicity |
| Example 20 | 0 | No phototoxicity |
| Example 21 | 0 | No phototoxicity |
| Example 22 | 0 | No phototoxicity |
| Example 23 | 0 | No phototoxicity |
| Example 24 | 0 | No phototoxicity |
| Example 25 | 0 | No phototoxicity |
| Example 26 | 0 | No phototoxicity |
| Example 27 | 0 | No phototoxicity |
| Example 28 | 0 | No phototoxicity |
| Example 29 | 0 | No phototoxicity |
| Example 30 | 0 | No phototoxicity |
| Example 31 | 0 | No phototoxicity |
| Example 32 | 0 | No phototoxicity |
| Example 33 | 0 | No phototoxicity |
| Example 34 | 0 | No phototoxicity |
| Example 35 | 0 | No phototoxicity |
| Example 36 | 0 | No phototoxicity |
| Example 37 | 0 | No phototoxicity |
| Example 38 | 0 | No phototoxicity |
| Example 39 | 0 | No phototoxicity |
| Example 40 | 0 | No phototoxicity |
| Example 41 | 0 | No phototoxicity |
| Example 42 | 0 | No phototoxicity |
| Example 43 | 0 | No phototoxicity |
| Example 44 | 0 | No phototoxicity |
| Example 45 | 0 | No phototoxicity |
| Example 46 | 0 | No phototoxicity |
| Example 47 | 0 | No phototoxicity |
| Example 48 | 0 | No phototoxicity |
| Example 49 | 0 | No phototoxicity |
| Example 50 | 0 | No phototoxicity |
| Example 51 | 0 | No phototoxicity |
| Example 52 | 0 | No phototoxicity |
| Example 53 | 0 | No phototoxicity |
| Example 54 | 0 | No phototoxicity |
| Example 55 | 0 | No phototoxicity |

As shown in Table 7, hydroxamic acid derivatives obtained in Examples 1 to 55 were confirmed to have 0 of phototoxic index, which was lower value than 0.5, criterion value to be estimated as no phototoxicity.

Hydroxamic acid derivatives according to the present invention may be incorporated into skin-care external compositions. The present composition may be formulated into, but not limited to, cosmetic compositions such as skin softners, astringents, nutrient toilet water, nutrient creams, massage creams, essences, eye creams, eye essences, cleansing creams, cleansing foams, cleansing water, packs, powders, body lotions, body creams, body oils, body essences, make-up bases, foundations, hairdyes, shampoos, hair-conditioners and body cleansers; and pharmaceutical compositions such as ointment, gels, creams, patches, and sprays. And, each formulation may further contain bases and additives suitable for the preparation thereof, if necessary, whose kind and amount can be easily selected in this art.

<Formulation 1> Nutrient Toilet Water (Milk Lotion)

Nutrient toilet water containing said hydroxamic acid derivatives obtained in Examples 1 to 55 was prepared.

| Ingredients | Amount (wt %) |
|---|---|
| 1. Distilled water | To 100 |
| 2. Glycerin | 8.0 |
| 3. Butylene glycol | 4.0 |
| 4. Extracts with hyaluronic acid | 5.0 |
| 5. β-glucan | 7.0 |
| 6. Carbomer | 0.1 |
| 7. Hydroxamic acid derivative | q.s. |
| 8. Caprylic/Capric triglyeride | 8.0 |
| 9. Squalane | 5.0 |
| 10. Cetearyl glucoside | 1.5 |
| 11. Sorbitan stearate | 0.4 |
| 12. Cetearyl alcohol | 1.0 |
| 13. Preservative | q.s. |
| 14. Perfume | q.s. |
| 15. Pigments | q.s. |
| 16. Triethanolamine | 0.1 |

<Formulation 2> Nutrient Cream

Nutrient cream containing said hydroxamic acid derivatives obtained in Examples 1 to 55 was prepared.

| Ingredients | Amount (wt %) |
|---|---|
| 1. Distilled water | To 100 |
| 2. Glycerin | 3.0 |
| 3. Butylene glycol | 3.0 |
| 4. Liquid paraffin | 7.0 |
| 5. β-glucan | 7.0 |
| 6. Carbomer | 0.1 |
| 7. Hydroxamic acid derivative | q.s. |
| 8. Caprylic/Capric triglyeride | 3.0 |
| 9. Squalane | 5.0 |
| 10. Cetearyl glucoside | 1.5 |
| 11. Sorbitan stearate | 0.4 |
| 12. Polysorbate 60 | 1.2 |
| 13. Preservative | q.s. |
| 14. Perfume | q.s. |
| 15. Pigments | q.s. |
| 16. Triethanolamine | 0.1 |

<Formulation 3> Massage Cream

Massage cream containing said hydroxamic acid derivatives obtained in Examples 1 to 55 was prepared.

| Ingredients | Amount (wt %) |
|---|---|
| 1. Distilled water | To 100 |
| 2. Glycerin | 8.0 |
| 3. Butylene glycol | 4.0 |
| 4. Liquid paraffin | 45.0 |
| 5. β-glucan | 7.0 |
| 6. Carbomer | 0.1 |
| 7. Hydroxamic acid derivative | q.s. |
| 8. Caprylic/Capric triglyeride | 3.0 |
| 9. Beeswax | 4.0 |
| 10. Cetearyl glucoside | 1.5 |
| 11. Sorbitan sesquioleate | 0.9 |
| 12. Vaseline | 3.0 |
| 13. Preservative | q.s. |
| 14. Perfume | q.s. |
| 15. Pigments | q.s. |
| 16. Paraffin | 1.5 |

<Formulation 4> Ointment

Ointment containing said hydroxamic acid derivatives obtained in Examples 1 to 55 was prepared.

| Ingredients | Amount (wt %) |
| --- | --- |
| 1. Distilled water | To 100 |
| 2. Glycerin | 8.0 |
| 3. Butylene glycol | 4.0 |
| 4. Liquid paraffin | 15.0 |
| 5. β-glucan | 7.0 |
| 6. Carbomer | 0.1 |
| 7. Hydroxamic acid derivative | q.s. |
| 8. Caprylic/Capric triglyeride | 3.0 |
| 9. Squalane | 1.0 |
| 10. Cetearyl glucoside | 1.5 |
| 11. Sorbitan stearate | 0.4 |
| 12. Cetearyl alcohol | 1.0 |
| 13. Preservative | q.s. |
| 14. Perfume | q.s. |
| 15. Pigments | q.s. |
| 16. Beeswax | 4.0 |

INDUSTRIAL APPLICATION OF THE INVENTION

As described in the above, hydroxamic acid derivatives according to the present invention can promote collagen biosynthesis and inhibit the expressions of collagenase and elastase by interacting to retinoic acid receptor. Furthermore, they do not cause skin irritation and skin toxicity, which have been drawbacks of retinoid compounds to be solved. Therefore, they can be incorporated into medicines or skin-care external compositions for improving skin elasticity and preventing skin aging.

The invention claimed is:

1. A hydroxamic acid derivative represented by the following formula(I):

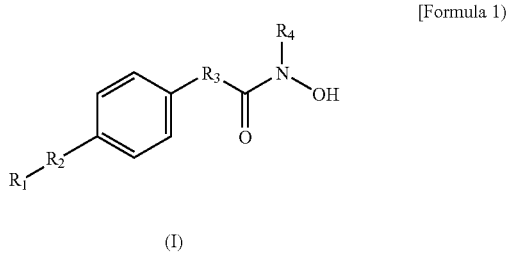

wherein, $R_1$ is

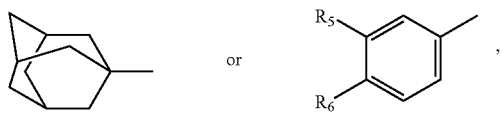

wherein, $R_5$ and $R_6$ each independently represents a hydrogen atom, an alkyl group having from 1 to 10 carbon atoms or a cyclic alkyl group having from 3 to 6 carbon atoms;

$R_2$ is CONH, NHCO, $CONR_7$ or $NR_7CO$, herein, $R_7$ represents an alkyl group having from 1 to 10 carbon atoms;

$R_3$ is —$(CH_2)_n$—, herein, n=0 or 1; and $R_4$ is a hydrogen atom or an alkyl group having from 1 to 10 carbon atoms;

on the proviso that compounds in which $R_1$ is

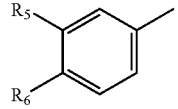

wherein $R_5$ and $R_6$ each are H, $R_2$ is CONH, and n=0, and compounds in which $R_1$ is

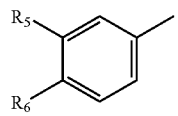

wherein $R_5$ is H and $R_6$ is $CH_3$, $R_2$ is CONH and n=0 or 1 are excluded.

2. The hydroxamic acid derivative according to claim 1, which is selected from the group consisting of N-[4-(N-hydroxycarbamoyl)phenyl]benzamide,
N-[4-(N-hydroxycarbamoyl)phenyl][3-methyiphenyl]carboxyamide,
N-[4-(N-hydroxycarbamoyl)phenyl][4-ethyiphenyl]carboxyamide,
N-[4-(N-hydroxycarbamoyl)phenyl][4-propyiphenyl]carboxyamide,
N-[4-(N-hydroxycarbamoyl)phenyl][4-isopropylphenyl]carboxyamide,
N-[4-(N-hydroxycarbamoyl)phenyl][4-butyiphenyl]carboxyamide,
N-[4-(N-hydroxycarbamoyl)phenyl][4-tert-butyiphenyl]carboxyamide,
N-[4-(N-hydroxycarbamoyl)phenyl][3,4-dimethylphenyl]carboxyamide,
N-[4-(N-hydroxycarbamoyl)phenyl]adamantyl carboxyamide, adamantyl-N-[4-(N-hydroxy-N-methylcarbamoyl)phenyl]carboxyamide,
N-[4-(N-hydroxycarbamoyl)phenyl]-N-methyl-benzamide,
N-[4-(N-hydroxycarbamoyl)phenyl]-N-methyl-[4-methyiphenyl]carboxyamide,
N-[4-(N-hydroxycarbamoyl)phenyl]-N-methyl-[3-methyiphenyl]carboxyamide,
N-[4-(N-hydroxycarbamoyl)phenyl]-N-methyl-[4-ethyiphenyl]carboxyamide,
N-[4-(N-hydroxycarbamoyl)phenyl]-N-methyl-[4-propyiphenyl]carboxyamide,
N-[4-(N-hydroxycarbamoyl)phenyl]-N-methyl-[4-isopropylphenyl]carboxyamide,
N-[4-(N-hydroxycarbamoyl)phenyl]-N-methyl-[4-butylphenyl]carboxyamide,
N-[4-(N-hydroxycarbamoyl)phenyl]-N-methyl-[4-tert-butylphenyl]carboxyamide,
N-[4-(N-hydroxycarbamoyl)phenyl]-N-methyl-[3,4-dimethylphenyl]carboxyamide,
N-[4-(N-hydroxycarbamoyl)phenyl]adamantyl-N-methylcarboxyamide, adamantyl-N-[4-(N-hydroxy-N-methylcarbamoyl)phenyl]-N-methylcarboxyamide,
N-[4-(N-hydroxycarbamoylmethyl)phenyl]beuzamide, N-[4-(N-hydroxycarbamoylmethyl)phenyl][3-methyiphenyl]carboxyamide,
N-[4-(N-hydroxycarbamoylmethyl)phenyl][4-ethyiphenyl]carboxyamide,
N-[4-(N-hydroxycarbamoylmethyl)phenyl][4-propyiphenyl]carboxyamide,
N-[4-(N-hydroxycarbamoylmethyl)phenyl][4-isopropyiphenyl]carboxyamide,
N-[4-(N-hydroxycarbamoylmethyl)phenyl][4-butyiphenyl]carboxyamide,
N-[4-(N-hydroxycarbamoylmethyl)phenyl][4-tert-butyiphenyl]carboxyamide,
N-[4-(N-hydroxycarbamoylmethyl)phenyl][3,4-dimethylphenyl]carboxyamide,
N-[4-(N-hydroxycarbamoylmethyl)phenyl]adamantyl carboxyamide,
2-[4-(adamantylcarbonylamino)phenyl]-N-hydroxy-N-methylacetamide,
[4-(N-hydroxycarbamoyl)phenyl]-N-[4-methyiphenyl] carboxyamide,
[4-(N-hydroxycarbamoyl)phenyl]-N-[3-methyiphenyl] carboxyamide,
[4-(N-hydroxycarbamoyl)phenyl]-N-[4-ethyiphenyl]carboxyamide,
[4-(N-hydroxycarbamoyl)phenyl]-N-[4-propylphenyl] carboxyamide,
[4-(N-hydroxycarbamoyl)phenyl]-N-[4-isopropylphenyl] carboxyamide,
[4-(N-hydroxycarbamoyl)phenyl]-N-[4-butyiphenyl]carboxyamide,
[4-(N-hydroxycarbamoyl)phenyl]-N-[4-tert-butyiphenyl] carboxyamide,
[4-(N-hydroxycarbamoyl)phenyl]-N-[3,4-dimethylphenyl]carboxyamide,
[4-(N-hydroxycarbamoyl)phenyl]-N-adamantyl carboxyamide,
N-adamantyl [4-(N-hydroxy-N-methylcarbamoyl)phenyl]carboxyamide,
[4-(N-hydroxycarbamoyl)phenyl]-N-methyl-N-benzamide,
[4-(N-hydroxycarbamoyl)phenyl]-N-methyl-N-[4-methyiphenyl]carboxyamide,
[4-(N-hydroxycarbamoyl)phenyl]-N-methyl-N-[3-methyiphenyl]carboxyamide,
[4-(N-hydroxycarbamoyl)phenyl]-N-methyl-N-[4-ethyiphenyl]carboxyamide,
[4-(N-hydroxycarbamoyl)phenyl]-N-methyl-N-[4-propyiphenyl]carboxyamide,
[4-(N-hydroxycarbamoyl)phenyl]-N-methyl-N-[4-isopropyiphenyl]carboxyamide,
[4-(N-hydroxycarbamoyl)phenyl]-N-methyl-N-[4-butylphenyl]carboxyamide,
[4-(N-hydroxycarbamoyl)phenyl]-N-methyl-N-[4-tert-butylphenyl]carboxyamide,
[4-(N-hydroxycarbamoyl)phenyl]-N-methyl-N-[3,4-dimethylphenyl]carboxyamide,
[4-(N-hydroxycarbamoyl)phenyl]-N-adamantyl-N-methylcarboxyamide, and
N-adamantyl [4-(N-hydroxy-N-methylcarbamoyl)phenyl]-N-methylcarboxyamide.

3. A method for preparing a hydroxamic acid represented by the following formula (I):

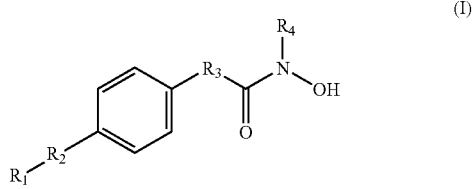

wherein
$R_1$ is

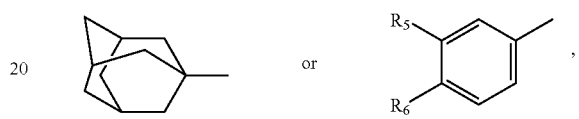

wherein, $R_5$ and $R_6$ each independently represents a hydrogen atom, an alkyl group having from 1 to 10 carbon atoms or a cyclic alkyl group having from 3 to 6 carbon atoms:
$R_2$ is CONH, NHCO. CONR$_7$ or NR$_7$CO, herein, $R_7$ represents an alkyl group having from 1 to 10 carbon atoms:
$R_3$ is —(CH$_2$)$_n$—, herein, n=0 or1: and
$R_4$ is a hydrogen atom or an alkyl group having from 1 to 10 carbon atoms:
on the proviso that compounds in which $R_1$ is

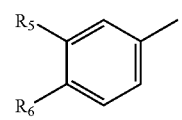

wherein $R_5$ and $R_6$ each are H,
$R_2$ is CONH, and n=0, and compounds in which $R_1$ is

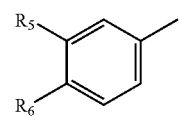

wherein $R_5$ is H and $R_6$ is CH$_3$, $R_2$ is CONH and n=0 or 1 are excluded, which comprises the steps of:
(a) reacting benzoic acid or adamantanecarboxylic acid with methyl 4-aminobenzoate or 4-aminophenylacetic acid methylester, to produce a benzamide compound;
(b) optionally, substituting an amide bond of the benzamide formed in step (a) with an alkyl group, to produce an akyl-substituted benzamide compound;
(c) hydrolyzing a methylester of the benzamide formed in step (a) or the alkyl-substituted benzamide compounds formed in step (b), to produce an acid; and
(d) reacting said acid with hydroxylamine hydrochloride or N-methyl hydroxylamine hydrochloride, to produce a hydroxamic acid derivative.

4. A method for preparing a hydroxamic acid derivative represented by the following formula (I):

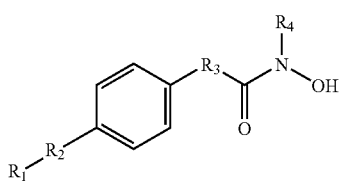

wherein,
R₁ is

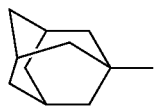 or 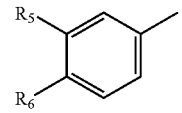, wherein, R₅ and R₆ each independently represents a hydrogen atom, an alkyl group having from 1 to 10 carbon atoms or a cyclic alkyl group having from 3 to 6 carbon atoms;
R₂ is CONH, NHCO, CONR₇ or NR₇CO, herein, R₇ represents an alkyl group having from 1 to 10 carbon atoms;
R₃ is —(CH₂)$_n$—, herein, n=0 or 1: and
R₄ is a hydrogen atom or an alkyl group having from 1 to 10 carbon atoms:
on the proviso that compounds in which R₁ is

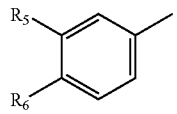

wherein R₅ and R₆ each are H,

R₂ is CONH, and n=0, and compounds in which R₁ is

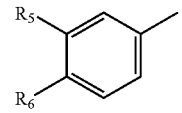

wherein R₅ is H and R₆ is CH₃,
R₂ is CONH and n=0 or 1 are excluded which comprises the steps of:
(a) reacting aniline or adamantamine with monomethyl-terephthalate, to produce a benzamide compound;
(b) optionally, substituting an amide bond of the benzamide formed in step (a) with an alkyl group, to produce an akyl-substituted benzamide compound
(c) hydrolyzing a methylester of the benzamide formed in step (a) or the alkyl-substituted benzamide compounds formed in step (b), to produce an acid; and
(d) reacting said acid with hydroxylamine hydrochloride or N-methyl hydroxylamine hydrochloride, to produce a hydroxamic acid derivative.

5. A skin-care external composition for preventing skin aging, containing the hydroxamic acid derivative according to claim 1 as an active ingredient.

6. A collagenase expression-inhibiting agent containing the hydroxamic acid derivative according to claim 1 as an active ingredient.

7. An elastase expression-inhibiting agent containing the hydroxamic acid derivative according to claim 1 as an active ingredient.

* * * * *